US010857029B2

(12) United States Patent
Ross et al.

(10) Patent No.: US 10,857,029 B2
(45) Date of Patent: Dec. 8, 2020

(54) VALVE SYSTEM OF SURGICAL CASSETTE MANIFOLD, SYSTEM, AND METHODS THEREOF

(71) Applicant: Johnson & Johnson Surgical Vision, Inc., Santa Ana, CA (US)

(72) Inventors: Mark W. Ross, Costa Mesa, CA (US); James B. Gerg, Lake Forest, CA (US)

(73) Assignee: Johnson & Johnson Surgical Vision, Inc., Santa Ana, CA (US)

( * ) Notice: Subject to any disclaimer, the term of this patent is extended or adjusted under 35 U.S.C. 154(b) by 393 days.

(21) Appl. No.: 14/940,004

(22) Filed: Nov. 12, 2015

(65) Prior Publication Data

US 2016/0067090 A1    Mar. 10, 2016

Related U.S. Application Data

(63) Continuation-in-part of application No. 14/686,582, filed on Apr. 14, 2015, now Pat. No. 10,219,938, which is a continuation-in-part of application No. 13/776,988, filed on Feb. 26, 2013, now Pat. No. 9,700,457.

(Continued)

(51) Int. Cl.
*A61F 9/007* (2006.01)
*A61F 9/008* (2006.01)
(Continued)

(52) U.S. Cl.
CPC .......... *A61F 9/00736* (2013.01); *A47B 81/00* (2013.01); *A61B 3/16* (2013.01);
(Continued)

(58) Field of Classification Search
CPC ...... A61M 2205/12; A61M 1/28; A61M 1/16; A61M 1/3621
See application file for complete search history.

(56) References Cited

U.S. PATENT DOCUMENTS 1,848,024 A    3/1932   Owen
2,123,781 A    7/1938   Huber
(Continued)

FOREIGN PATENT DOCUMENTS

AU    2006235983 A1    5/2007
DE         3311104 A1 *  9/1984  .............. F04B 43/02
(Continued)

OTHER PUBLICATIONS

International Search Report and Written Opinion for Application No. PCT/US2016/049970, dated Dec. 5, 2016, 12 pages.

(Continued)

*Primary Examiner* — Scott J Medway
(74) *Attorney, Agent, or Firm* — Johnson & Johnson Surgical Vision, Inc.

(57) ABSTRACT

A surgical system includes a replaceable surgical cassette that is configured to be received by a surgical console, the surgical cassette permitting fluid flow through the cassette, the surgical system controlling the flow of fluid through the cassette via one or more flexible valves actuated by one or more actuation plungers located on the surgical console. The one or more flexible valves of the surgical cassette and the one or more actuation plungers of the surgical console include a positioning feature configured to assist with positioning the one or more actuation plungers to apply uniform and symmetric pressure to the one or more valves during actuation.

9 Claims, 16 Drawing Sheets

Related U.S. Application Data

(60) Provisional application No. 61/612,307, filed on Mar. 17, 2012.

(51) Int. Cl.
  *A61M 1/00* (2006.01)
  *A61M 3/02* (2006.01)
  *A61B 3/16* (2006.01)
  *A47B 81/00* (2006.01)

(52) U.S. Cl.
  CPC ............ *A61F 9/007* (2013.01); *A61F 9/008* (2013.01); *A61F 9/00745* (2013.01); *A61M 1/0023* (2013.01); *A61M 1/0058* (2013.01); *A61M 3/022* (2014.02); *A61M 3/0216* (2014.02); *A61M 1/0025* (2014.02); *A61M 3/0258* (2013.01); *A61M 2205/12* (2013.01); *A61M 2205/121* (2013.01); *A61M 2205/123* (2013.01); *A61M 2205/128* (2013.01); *A61M 2205/3331* (2013.01); *A61M 2205/3379* (2013.01); *A61M 2205/505* (2013.01); *A61M 2210/0612* (2013.01); *Y10T 29/49826* (2015.01)

(56) References Cited

U.S. PATENT DOCUMENTS

| | | | |
|---|---|---|---|
| 2,211,167 A * | 8/1940 | Safford | F16K 7/16 251/262 |
| 2,514,882 A * | 7/1950 | Leiman | F16N 7/02 184/66 |
| 2,869,571 A * | 1/1959 | Price | F16K 31/20 137/215 |
| 2,990,616 A | 7/1961 | Balamuth et al. | |
| 3,019,815 A * | 2/1962 | Lenardon | A01K 63/042 137/883 |
| 3,076,904 A | 2/1963 | Claus et al. | |
| 3,116,697 A | 1/1964 | Theodore | |
| 3,203,186 A * | 8/1965 | Sheppard | F15B 7/005 60/534 |
| 3,366,100 A * | 1/1968 | Sapp | F01M 1/24 123/198 DC |
| 3,439,680 A | 4/1969 | Thomas, Jr. | |
| 3,515,169 A * | 6/1970 | Dobrikin | F16K 15/14 137/625.25 |
| 3,526,219 A | 9/1970 | Lewis | |
| 3,781,142 A | 12/1973 | Zweig | |
| 3,850,265 A * | 11/1974 | Blower | F16K 31/1266 184/7.4 |
| 3,857,387 A | 12/1974 | Shock | |
| 3,913,895 A * | 10/1975 | De Bruyne | A47J 43/09 366/247 |
| 4,017,828 A | 4/1977 | Watanabe et al. | |
| 4,037,491 A | 7/1977 | Newbold | |
| 4,121,584 A * | 10/1978 | Turner | A61M 5/16809 604/246 |
| 4,189,286 A | 2/1980 | Murry et al. | |
| 4,193,004 A | 3/1980 | Lobdell et al. | |
| 4,247,784 A | 1/1981 | Henry | |
| 4,276,023 A | 6/1981 | Phillips et al. | |
| 4,286,464 A | 9/1981 | Tauber et al. | |
| 4,479,760 A | 10/1984 | Bilstad et al. | |
| 4,537,561 A | 8/1985 | Xanthopoulos | |
| 4,564,342 A | 1/1986 | Weber et al. | |
| 4,590,934 A | 5/1986 | Malis et al. | |
| 4,662,829 A | 5/1987 | Nehring | |
| 4,665,621 A | 5/1987 | Ackerman et al. | |
| 4,706,687 A | 11/1987 | Rogers et al. | |
| 4,713,051 A | 12/1987 | Steppe et al. | |
| 4,757,814 A | 7/1988 | Wang et al. | |
| 4,758,220 A | 7/1988 | Sundblom et al. | |
| 4,758,238 A * | 7/1988 | Sundblom | A61M 1/0001 604/153 |
| 4,772,263 A | 9/1988 | Dorman et al. | |
| 4,773,897 A | 9/1988 | Scheller et al. | |
| 4,818,186 A | 4/1989 | Pastrone et al. | |
| 4,819,317 A | 4/1989 | Bauer et al. | |
| 4,837,857 A | 6/1989 | Scheller et al. | |
| 4,920,336 A | 4/1990 | Meijer | |
| 4,921,477 A | 5/1990 | Davis | |
| 4,925,444 A | 5/1990 | Orkin et al. | |
| 4,933,843 A | 6/1990 | Scheller et al. | |
| 4,941,518 A | 7/1990 | Williams et al. | |
| 4,954,960 A | 9/1990 | Lo et al. | |
| 4,961,424 A | 10/1990 | Kubota et al. | |
| 4,965,417 A | 10/1990 | Massie | |
| 4,983,901 A | 1/1991 | Lehmer | |
| 4,998,972 A | 3/1991 | Chin et al. | |
| 5,006,110 A | 4/1991 | Garrison et al. | |
| 5,020,535 A | 6/1991 | Parker et al. | |
| 5,026,387 A | 6/1991 | Thomas | |
| 5,032,939 A | 7/1991 | Mihara et al. | |
| 5,039,973 A | 8/1991 | Carballo | |
| 5,091,656 A | 2/1992 | Gahn | |
| 5,108,367 A | 4/1992 | Epstein et al. | |
| 5,110,270 A | 5/1992 | Morrick | |
| 5,125,891 A | 6/1992 | Hossain | |
| 5,160,317 A | 11/1992 | Costin | |
| 5,195,960 A | 3/1993 | Hossain | |
| 5,195,961 A | 3/1993 | Takahashi et al. | |
| 5,195,971 A | 3/1993 | Sirhan | |
| 5,230,614 A | 7/1993 | Zanger et al. | |
| 5,242,404 A | 9/1993 | Conley et al. | |
| 5,249,121 A | 9/1993 | Baum et al. | |
| 5,267,956 A | 12/1993 | Beuchat | |
| 5,268,624 A | 12/1993 | Zanger | |
| 5,271,379 A | 12/1993 | Phan et al. | |
| 5,273,517 A | 12/1993 | Barone et al. | |
| 5,282,787 A | 2/1994 | Wortrich | |
| 5,323,543 A | 6/1994 | Steen et al. | |
| 5,342,293 A | 8/1994 | Zanger | |
| 5,344,292 A * | 9/1994 | Rabenau | F04B 43/02 417/360 |
| 5,350,357 A | 9/1994 | Kamen et al. | |
| 5,351,676 A | 10/1994 | Putman | |
| 5,378,126 A * | 1/1995 | Abrahamson | A61M 5/14224 417/413.1 |
| 5,388,569 A | 2/1995 | Kepley | |
| 5,429,601 A | 7/1995 | Conley et al. | |
| 5,445,506 A | 8/1995 | Afflerbaugh et al. | |
| 5,454,783 A | 10/1995 | Grieshaber et al. | |
| 5,464,391 A | 11/1995 | Devale | |
| 5,470,211 A | 11/1995 | Knott et al. | |
| 5,470,312 A | 11/1995 | Zanger et al. | |
| 5,499,969 A | 3/1996 | Beuchat et al. | |
| 5,520,652 A | 5/1996 | Peterson | |
| 5,533,976 A | 7/1996 | Zaleski et al. | |
| 5,549,461 A | 8/1996 | Newland | |
| 5,554,894 A | 9/1996 | Sepielli | |
| 5,561,575 A | 10/1996 | Eways | |
| 5,569,188 A | 10/1996 | Mackool | |
| 5,580,347 A | 12/1996 | Reimels | |
| 5,591,127 A | 1/1997 | Barwick et al. | |
| 5,653,887 A | 8/1997 | Wahl et al. | |
| 5,657,000 A | 8/1997 | Ellingboe | |
| 5,676,530 A | 10/1997 | Nazarifar | |
| 5,676,649 A | 10/1997 | Boukhny et al. | |
| 5,676,650 A | 10/1997 | Grieshaber et al. | |
| 5,693,020 A | 12/1997 | Rauh | |
| 5,697,898 A | 12/1997 | Devine | |
| 5,697,910 A | 12/1997 | Cole et al. | |
| 5,700,240 A | 12/1997 | Barwick, Jr. et al. | |
| 5,724,264 A | 3/1998 | Rosenberg et al. | |
| 5,728,130 A | 3/1998 | Ishikawa et al. | |
| 5,733,256 A | 3/1998 | Costin | |
| 5,733,263 A | 3/1998 | Wheatman | |
| 5,745,647 A | 4/1998 | Krause | |
| 5,746,713 A | 5/1998 | Hood et al. | |
| 5,747,824 A | 5/1998 | Jung et al. | |
| 5,777,602 A | 7/1998 | Schaller et al. | |
| 5,805,998 A | 9/1998 | Kodama | |
| 5,807,075 A | 9/1998 | Jacobsen et al. | |

(56) References Cited

U.S. PATENT DOCUMENTS

| | | | |
|---|---|---|---|
| 5,810,765 A | 9/1998 | Oda | |
| 5,810,766 A | 9/1998 | Barnitz et al. | |
| 5,830,176 A | 11/1998 | Mackool | |
| 5,843,109 A | 12/1998 | Mehta et al. | |
| 5,859,642 A | 1/1999 | Jones | |
| 5,871,492 A | 2/1999 | Sorensen | |
| 5,879,298 A | 3/1999 | Drobnitzky et al. | |
| 5,883,615 A | 3/1999 | Fago et al. | |
| 5,899,674 A | 5/1999 | Jung et al. | |
| 5,928,257 A | 7/1999 | Kablik et al. | |
| 5,938,655 A | 8/1999 | Bisch et al. | |
| 5,983,749 A | 11/1999 | Holtorf | |
| 6,002,484 A | 12/1999 | Rozema et al. | |
| 6,024,428 A | 2/2000 | Uchikata | |
| 6,028,387 A | 2/2000 | Boukhny | |
| 6,062,829 A | 5/2000 | Ognier | |
| 6,065,389 A * | 5/2000 | Riedlinger | F04B 43/0054 92/99 |
| 6,077,285 A | 6/2000 | Boukhny | |
| 6,086,598 A | 7/2000 | Appelbaum et al. | |
| 6,109,895 A | 8/2000 | Ray et al. | |
| 6,117,126 A | 9/2000 | Appelbaum et al. | |
| 6,139,320 A | 10/2000 | Hahn | |
| 6,150,623 A | 11/2000 | Chen | |
| 6,159,175 A | 12/2000 | Strukel et al. | |
| 6,179,829 B1 | 1/2001 | Bisch et al. | |
| 6,187,182 B1 * | 2/2001 | Reynolds | B01D 46/0004 210/136 |
| 6,200,287 B1 | 3/2001 | Keller et al. | |
| 6,219,032 B1 | 4/2001 | Rosenberg et al. | |
| 6,251,113 B1 | 6/2001 | Appelbaum et al. | |
| 6,260,434 B1 | 7/2001 | Holtorf | |
| 6,360,630 B2 | 3/2002 | Holtorf | |
| 6,368,269 B1 | 4/2002 | Lane | |
| 6,411,062 B1 | 6/2002 | Baranowski et al. | |
| 6,424,124 B2 | 7/2002 | Ichihara et al. | |
| 6,436,072 B1 | 8/2002 | Kullas et al. | |
| 6,452,120 B1 | 9/2002 | Chen | |
| 6,452,123 B1 | 9/2002 | Chen | |
| 6,491,661 B1 | 12/2002 | Boukhny et al. | |
| 6,511,454 B1 | 1/2003 | Nakao et al. | |
| 6,537,445 B2 | 3/2003 | Muller | |
| 6,561,999 B1 | 5/2003 | Nazarifar et al. | |
| 6,595,948 B2 | 7/2003 | Suzuki et al. | |
| 6,632,214 B2 | 10/2003 | Morgan et al. | |
| 6,674,030 B2 | 1/2004 | Chen et al. | |
| 6,830,555 B2 | 12/2004 | Rockley et al. | |
| 6,852,092 B2 | 2/2005 | Kadziauskas et al. | |
| 6,862,951 B2 | 3/2005 | Peterson et al. | |
| 6,908,451 B2 | 6/2005 | Brody et al. | |
| 6,962,488 B2 | 11/2005 | Davis et al. | |
| 6,962,581 B2 | 11/2005 | Thoe | |
| 6,986,753 B2 | 1/2006 | Bui | |
| 7,011,761 B2 | 3/2006 | Muller | |
| 7,012,203 B2 | 3/2006 | Hanson et al. | |
| 7,070,578 B2 | 7/2006 | Leukanech et al. | |
| 7,073,083 B2 | 7/2006 | Litwin, Jr. et al. | |
| 7,087,049 B2 | 8/2006 | Nowlin et al. | |
| 7,103,344 B2 | 9/2006 | Menard | |
| 7,167,723 B2 | 1/2007 | Zhang | |
| 7,169,123 B2 | 1/2007 | Kadziauskas et al. | |
| 7,236,766 B2 | 6/2007 | Freeburg | |
| 7,236,809 B2 | 6/2007 | Fischedick et al. | |
| 7,242,765 B2 | 7/2007 | Hairston | |
| 7,244,240 B2 | 7/2007 | Nazarifar et al. | |
| 7,289,825 B2 | 10/2007 | Fors et al. | |
| 7,300,264 B2 | 11/2007 | Souza | |
| 7,316,664 B2 | 1/2008 | Kadziauskas et al. | |
| 7,336,976 B2 | 2/2008 | Ito | |
| 7,381,917 B2 | 6/2008 | Dacquay et al. | |
| 7,439,463 B2 | 10/2008 | Brenner et al. | |
| 7,465,285 B2 | 12/2008 | Hutchinson et al. | |
| 7,470,277 B2 | 12/2008 | Finlay et al. | |
| 7,526,038 B2 | 4/2009 | McNamara | |
| 7,591,639 B2 | 9/2009 | Kent | |
| 7,731,484 B2 | 6/2010 | Yamamoto et al. | |
| 7,776,006 B2 | 8/2010 | Childers et al. | |
| 7,785,316 B2 | 8/2010 | Claus et al. | |
| 7,811,255 B2 | 10/2010 | Boukhny et al. | |
| 7,883,521 B2 | 2/2011 | Rockley et al. | |
| 7,921,017 B2 | 4/2011 | Claus et al. | |
| 7,967,777 B2 | 6/2011 | Edwards et al. | |
| 8,015,912 B2 * | 9/2011 | Stimpson | F04B 53/22 92/99 |
| 8,070,712 B2 | 12/2011 | Muri et al. | |
| 8,075,468 B2 | 12/2011 | Min et al. | |
| 9,033,940 B2 | 5/2015 | Muri et al. | |
| 9,180,240 B2 * | 11/2015 | Farrell | A61M 1/28 |
| 9,500,188 B2 * | 11/2016 | Ly | F04B 17/042 |
| 9,658,468 B2 | 5/2017 | Dai | |
| 10,330,094 B2 * | 6/2019 | Gledhill, III | B29C 45/14311 |
| 2001/0023331 A1 | 9/2001 | Kanda et al. | |
| 2001/0047166 A1 | 11/2001 | Wuchinich | |
| 2001/0051788 A1 | 12/2001 | Paukovits et al. | |
| 2002/0004657 A1 | 1/2002 | Morgan et al. | |
| 2002/0007671 A1 | 1/2002 | Lavi et al. | |
| 2002/0019215 A1 | 2/2002 | Romans | |
| 2002/0045887 A1 | 4/2002 | Dehoogh et al. | |
| 2002/0070840 A1 | 6/2002 | Fischer et al. | |
| 2002/0098859 A1 | 7/2002 | Murata | |
| 2002/0137007 A1 | 9/2002 | Beerstecher | |
| 2002/0179462 A1 | 12/2002 | Silvers | |
| 2002/0183693 A1 | 12/2002 | Peterson et al. | |
| 2003/0028091 A1 | 2/2003 | Simon et al. | |
| 2003/0050619 A1 | 3/2003 | Mooijman et al. | |
| 2003/0083016 A1 | 5/2003 | Evans et al. | |
| 2003/0108429 A1 | 6/2003 | Angelini et al. | |
| 2003/0125717 A1 | 7/2003 | Whitman | |
| 2003/0224729 A1 | 12/2003 | Arnold | |
| 2003/0226091 A1 | 12/2003 | Platenberg et al. | |
| 2004/0019313 A1 | 1/2004 | Childers et al. | |
| 2004/0037724 A1 | 2/2004 | Haser et al. | |
| 2004/0097868 A1 | 5/2004 | Kadziauskas et al. | |
| 2004/0127840 A1 * | 7/2004 | Gara | A61M 1/3683 604/4.01 |
| 2004/0193182 A1 | 9/2004 | Yaguchi et al. | |
| 2004/0212344 A1 | 10/2004 | Tamura et al. | |
| 2004/0215127 A1 | 10/2004 | Kadziauskas et al. | |
| 2004/0224641 A1 | 11/2004 | Sinn | |
| 2004/0253129 A1 | 12/2004 | Sorensen et al. | |
| 2005/0039567 A1 | 2/2005 | Peterson et al. | |
| 2005/0054971 A1 | 3/2005 | Steen et al. | |
| 2005/0069419 A1 | 3/2005 | Cull et al. | |
| 2005/0070859 A1 | 3/2005 | Cull et al. | |
| 2005/0070871 A1 | 3/2005 | Lawton et al. | |
| 2005/0095153 A1 | 5/2005 | Demers et al. | |
| 2005/0103607 A1 | 5/2005 | Mezhinsky | |
| 2005/0109595 A1 | 5/2005 | Mezhinsky et al. | |
| 2005/0118048 A1 | 6/2005 | Traxinger | |
| 2005/0119679 A1 | 6/2005 | Rabiner et al. | |
| 2005/0130098 A1 | 6/2005 | Warner | |
| 2005/0187513 A1 | 8/2005 | Rabiner et al. | |
| 2005/0197131 A1 | 9/2005 | Ikegami | |
| 2005/0209552 A1 | 9/2005 | Beck et al. | |
| 2005/0228266 A1 | 10/2005 | McCombs | |
| 2005/0236936 A1 | 10/2005 | Shiv et al. | |
| 2005/0245888 A1 | 11/2005 | Cull | |
| 2005/0261628 A1 | 11/2005 | Boukhny et al. | |
| 2005/0267504 A1 | 12/2005 | Boukhny et al. | |
| 2006/0035585 A1 | 2/2006 | Washiro | |
| 2006/0036180 A1 | 2/2006 | Boukhny et al. | |
| 2006/0041220 A1 | 2/2006 | Boukhny et al. | |
| 2006/0046659 A1 | 3/2006 | Haartsen et al. | |
| 2006/0074405 A1 | 4/2006 | Malackowski et al. | |
| 2006/0078448 A1 | 4/2006 | Holden | |
| 2006/0114175 A1 | 6/2006 | Boukhny | |
| 2006/0145540 A1 | 7/2006 | Mezhinsky | |
| 2006/0219049 A1 | 10/2006 | Horvath et al. | |
| 2006/0219962 A1 | 10/2006 | Dancs et al. | |
| 2006/0224107 A1 | 10/2006 | Claus et al. | |
| 2006/0236242 A1 | 10/2006 | Boukhny et al. | |
| 2007/0016174 A1 | 1/2007 | Millman et al. | |
| 2007/0049898 A1 | 3/2007 | Hopkins et al. | |
| 2007/0060926 A1 | 3/2007 | Escaf | |

(56) References Cited

U.S. PATENT DOCUMENTS

| | | |
|---|---|---|
| 2007/0073214 A1 | 3/2007 | Dacquay et al. |
| 2007/0073309 A1 | 3/2007 | Kadziauskas et al. |
| 2007/0078379 A1 | 4/2007 | Boukhny et al. |
| 2007/0085611 A1 | 4/2007 | Gerry et al. |
| 2007/0107490 A1 | 5/2007 | Artsyukhovich et al. |
| 2007/0231205 A1 | 10/2007 | Williams et al. |
| 2007/0249942 A1 | 10/2007 | Salehi et al. |
| 2007/0287959 A1 | 12/2007 | Walter et al. |
| 2008/0033342 A1 | 2/2008 | Staggs |
| 2008/0066542 A1 | 3/2008 | Gao |
| 2008/0082040 A1 | 4/2008 | Kubler et al. |
| 2008/0082077 A1 | 4/2008 | Williams |
| 2008/0112828 A1 | 5/2008 | Muri et al. |
| 2008/0114290 A1 | 5/2008 | King et al. |
| 2008/0114291 A1 | 5/2008 | Muri et al. |
| 2008/0114300 A1 | 5/2008 | Muri et al. |
| 2008/0114311 A1 | 5/2008 | Muri et al. |
| 2008/0114312 A1* | 5/2008 | Muri .................. A61M 1/0058 604/294 |
| 2008/0114387 A1 | 5/2008 | Hertweck et al. |
| 2008/0125695 A1 | 5/2008 | Hopkins et al. |
| 2008/0125697 A1 | 5/2008 | Gao |
| 2008/0125698 A1 | 5/2008 | Gerg et al. |
| 2008/0129695 A1 | 6/2008 | Li |
| 2008/0146989 A1 | 6/2008 | Zacharias |
| 2008/0200878 A1 | 8/2008 | Davis et al. |
| 2008/0243105 A1 | 10/2008 | Horvath |
| 2008/0262476 A1 | 10/2008 | Krause et al. |
| 2008/0281253 A1 | 11/2008 | Injev et al. |
| 2008/0294087 A1 | 11/2008 | Steen et al. |
| 2008/0312594 A1 | 12/2008 | Urich et al. |
| 2009/0005712 A1 | 1/2009 | Raney |
| 2009/0005789 A1 | 1/2009 | Charles |
| 2009/0048607 A1 | 2/2009 | Rockley |
| 2009/0087327 A1 | 4/2009 | Voltenburg, Jr. et al. |
| 2009/0124974 A1 | 5/2009 | Crank et al. |
| 2009/0163853 A1 | 6/2009 | Cull et al. |
| 2010/0036256 A1 | 2/2010 | Boukhny et al. |
| 2010/0069825 A1 | 3/2010 | Raney |
| 2010/0069828 A1 | 3/2010 | Steen et al. |
| 2010/0140149 A1 | 6/2010 | Fulkerson et al. |
| 2010/0152685 A1* | 6/2010 | Goh ................... A61M 1/0031 604/319 |
| 2010/0185150 A1 | 7/2010 | Zacharias |
| 2010/0249693 A1 | 9/2010 | Links |
| 2010/0280435 A1 | 11/2010 | Raney et al. |
| 2011/0092887 A1 | 4/2011 | Wong et al. |
| 2011/0092924 A1 | 4/2011 | Wong et al. |
| 2011/0092962 A1 | 4/2011 | Ma et al. |
| 2011/0098721 A1 | 4/2011 | Tran et al. |
| 2011/0160646 A1 | 6/2011 | Kadziauskas et al. |
| 2011/0208047 A1 | 8/2011 | Fago |
| 2011/0251569 A1 | 10/2011 | Turner et al. |
| 2012/0065580 A1 | 3/2012 | Gerg et al. |
| 2012/0078181 A1 | 3/2012 | Smith et al. |
| 2012/0083735 A1 | 4/2012 | Pfouts |
| 2012/0083736 A1 | 4/2012 | Pfouts et al. |
| 2012/0083800 A1 | 4/2012 | Andersohn |
| 2013/0072853 A1 | 3/2013 | Wong et al. |
| 2013/0169412 A1 | 7/2013 | Roth |
| 2013/0184638 A1* | 7/2013 | Scarpaci .............. A61M 1/166 604/28 |
| 2013/0184676 A1 | 7/2013 | Kamen et al. |
| 2013/0245543 A1 | 9/2013 | Gerg et al. |
| 2013/0289475 A1 | 10/2013 | Muri et al. |
| 2013/0303978 A1 | 11/2013 | Ross |
| 2013/0336814 A1 | 12/2013 | Kamen et al. |
| 2014/0178215 A1 | 6/2014 | Baxter et al. |
| 2014/0188076 A1 | 7/2014 | Kamen et al. |
| 2014/0276424 A1 | 9/2014 | Davis et al. |
| 2016/0151564 A1 | 6/2016 | Magers et al. |

FOREIGN PATENT DOCUMENTS

| | | | |
|---|---|---|---|
| DE | 3826414 A1 | 2/1989 | |
| EP | 56019 A1 | 7/1982 | |
| EP | 424687 A1 | 5/1991 | |
| EP | 619993 A1 | 10/1994 | |
| EP | 1010437 A1 | 6/2000 | |
| EP | 1072285 A1 | 1/2001 | |
| EP | 1113562 A1 | 7/2001 | |
| EP | 1464310 A1 | 10/2004 | |
| EP | 1469440 A2 | 10/2004 | |
| EP | 1550406 A2 | 7/2005 | |
| EP | 1704839 A1 | 9/2006 | |
| EP | 1779879 A1 | 5/2007 | |
| EP | 1787606 A1 | 5/2007 | |
| EP | 1849443 A1 | 10/2007 | |
| EP | 1849444 A1 | 10/2007 | |
| EP | 1857128 A1 | 11/2007 | |
| EP | 1310267 B1 | 1/2008 | |
| EP | 1873501 A1 | 1/2008 | |
| EP | 1900347 A1 | 3/2008 | |
| EP | 1925274 A2 | 5/2008 | |
| EP | 1867349 B1 | 11/2008 | |
| ES | 2264369 A1 | 12/2006 | |
| GB | 2230301 A | 10/1990 | |
| GB | 2352887 A | 2/2001 | |
| GB | 2438679 A | 12/2007 | |
| JP | S5724482 A | 2/1982 | |
| JP | S58167333 A | 10/1983 | |
| JP | S62204463 A | 9/1987 | |
| JP | 2005195653 A | 7/2005 | |
| JP | 2008188110 A | 8/2008 | |
| WO | 9220310 A1 | 11/1992 | |
| WO | 9315777 A2 | 8/1993 | |
| WO | 9317729 A1 | 9/1993 | |
| WO | 9324082 A1 | 12/1993 | |
| WO | WO-9324082 A1 * | 12/1993 | ......... A61F 9/00736 |
| WO | 9405346 A1 | 3/1994 | |
| WO | 9632144 A1 | 10/1996 | |
| WO | 9737700 A1 | 10/1997 | |
| WO | 9818507 A1 | 5/1998 | |
| WO | 9917818 A1 | 4/1999 | |
| WO | 0000096 A1 | 1/2000 | |
| WO | 0070225 A1 | 11/2000 | |
| WO | 0122696 A1 | 3/2001 | |
| WO | 0226286 A2 | 4/2002 | |
| WO | 0228449 A2 | 4/2002 | |
| WO | 0234314 A1 | 5/2002 | |
| WO | 03102878 A1 | 12/2003 | |
| WO | 04096360 A1 | 11/2004 | |
| WO | 2004114180 A1 | 12/2004 | |
| WO | 05084728 A2 | 9/2005 | |
| WO | 05092023 A2 | 10/2005 | |
| WO | 05092047 A2 | 10/2005 | |
| WO | 06101908 A2 | 9/2006 | |
| WO | 06125280 A1 | 11/2006 | |
| WO | 2007121144 A1 | 10/2007 | |
| WO | 2007143677 A2 | 12/2007 | |
| WO | 2007143797 A1 | 12/2007 | |
| WO | 2007149637 A2 | 12/2007 | |
| WO | 2008030872 A1 | 3/2008 | |
| WO | 2008060859 A1 | 5/2008 | |
| WO | 2008060902 A1 | 5/2008 | |
| WO | 2008060995 A1 | 5/2008 | |
| WO | 2009123547 A1 | 10/2009 | |
| WO | 2010054146 A1 | 5/2010 | |
| WO | 2010054225 A2 | 5/2010 | |
| WO | 2010151704 A1 | 12/2010 | |
| WO | 2012006425 A2 | 1/2012 | |
| WO | 2012151062 A1 | 11/2012 | |
| WO | 2013142009 A1 | 9/2013 | |
| WO | 2015009945 A1 | 1/2015 | |

OTHER PUBLICATIONS

International Search Report and Written Opinion for Application No. PCT/US2015/066036, dated Jul. 4, 2016, 20 pages.

(56) References Cited

OTHER PUBLICATIONS

Boyd, "Preparing for the Transition" in: The Art and the Science of Cataract Surgery, Chapter 7, 2001, pp. 93-133.
Definition of "Parameter", Retrieved from the Internet.
English Human Translation of JP57024482 from Feb. 9, 1982.
European Search Report for Application No. EP10164058, dated Jun. 25, 2010, 2 pages.
European Search Report for Application No. EP13184138.9, dated Oct. 24, 2013, 7 pages.
Examination Report dated Mar. 28, 2012 for European Application No. EP09791072 filed Jul. 31, 2009, 3 pages.
Merritt R., et al., Wireless Nets Starting to link Medical Gear [online] 2004 [retrieved on Feb. 12, 2007]. Retrieved from the Internet.
Phacoemulsification, [online] [retrieved on Jul. 1, 2009]. Retrieved from the Internet: , 2 pages.
International Search Report and Written Opinion for Application No. PCT/US2016/061648, dated Feb. 7, 2017, 12 pages.

\* cited by examiner

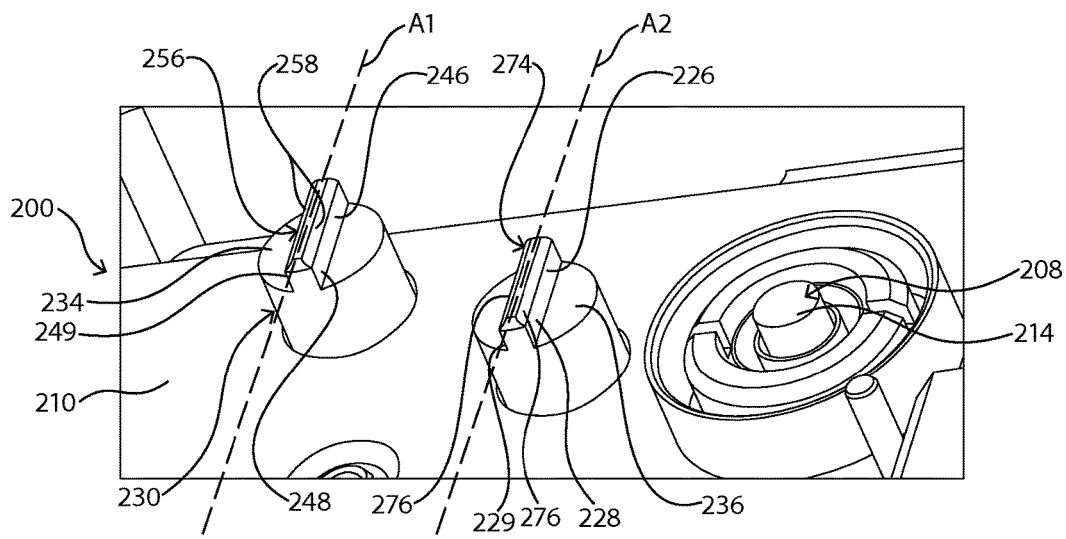
FIG. 10A
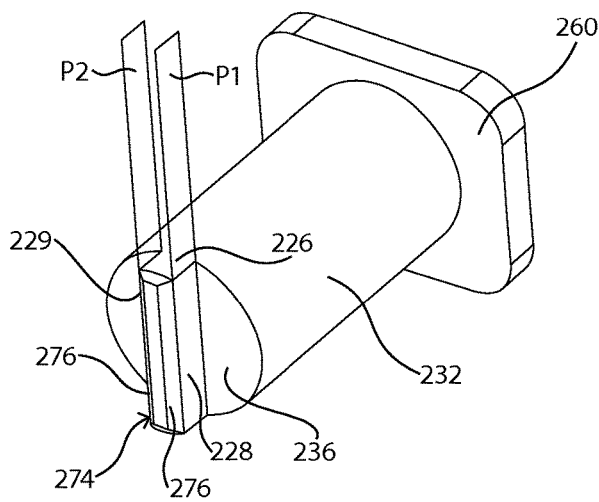
FIG. 10B1
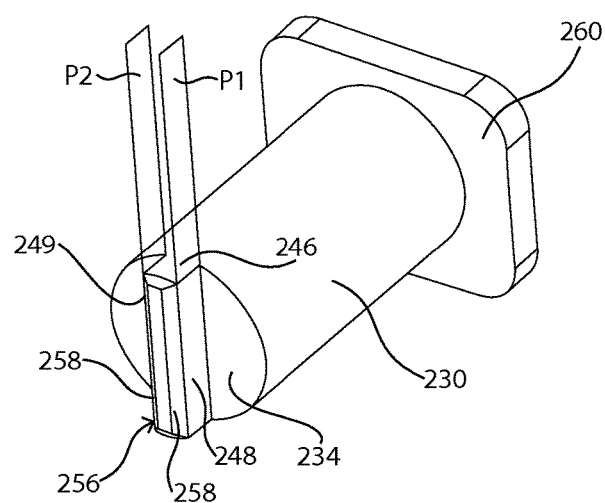
FIG. 10B2

VALVE SYSTEM OF SURGICAL CASSETTE MANIFOLD, SYSTEM, AND METHODS THEREOF

CROSS-REFERENCE TO RELATED APPLICATIONS

This application claims priority to and is a continuation-in-part application of U.S. application Ser. No. 14/686,582 filed on Apr. 14, 2015, which claims priority to and is a continuation-in-part of U.S. application Ser. No. 13/776,988 filed on Feb. 26, 2013, which claims priority to U.S. provisional application No. 61/612,307 filed on Mar. 17, 2012, the contents of each are hereby incorporated by reference in their entirety.

TECHNICAL FIELD OF THE INVENTION

The present invention is generally related to methods, devices, and systems for controlling surgical fluid flows, particularly during treatment of an eye. More particularly, the present invention generally relates to methods, devices and systems associated with a valve system of a removable cassette for controlling surgical fluid flows.

BACKGROUND OF THE INVENTION

The optical elements of the eye include both a cornea (at the front of the eye) and a lens within the eye. The lens and cornea work together to focus light onto the retina at the back of the eye. The lens also changes in shape, adjusting the focus of the eye to vary between viewing near objects and far objects. The lens is found just behind the pupil, and within a capsular bag. This capsular bag is a thin, relatively delicate structure which separates the eye into anterior and posterior chambers.

With age, clouding of the lens or cataracts are fairly common. Cataracts may form in the hard central nucleus of the lens, in the softer peripheral cortical portion of the lens, or at the back of the lens near the capsular bag.

Cataracts can be treated by the replacement of the cloudy lens with an artificial lens. Phacoemulsification systems often use ultrasound energy to fragment the lens and aspirate the lens material from within the capsular bag. This may allow the capsular bag to be used for positioning of the artificial lens, and maintains the separation between the anterior portion of the eye and the vitreous humour in the posterior chamber of the eye.

During cataract surgery and other therapies of the eye, accurate control over the volume of fluid within the eye is highly beneficial. For example, while ultrasound energy breaks up the lens and allows it to be drawn into a treatment probe with an aspiration flow, a corresponding irrigation flow may be introduced into the eye so that the total volume of fluid in the eye does not change excessively. If the total volume of fluid in the eye is allowed to get too low at any time during the procedure, the eye may collapse and cause significant tissue damage. Similarly, excessive pressure within the eye may strain and injure tissues of the eye.

While a variety of specific fluid transport mechanisms have been used in phacoemulsification and other treatment systems for the eyes, aspiration flow systems can generally be classified in two categories: 1) volumetric-based aspiration flow systems using positive displacement pumps; and 2) vacuum-based aspiration systems using a vacuum source, typically applied to the aspiration flow through an air-liquid interface. These two categories of aspiration flow systems each have unique characteristics that render one more suitable for some procedures than the other, and vice versa.

Among positive displacement aspiration systems, peristaltic pumps (which use rotating rollers that press against a flexible tubing to induce flow) are commonly employed. Such pumps provide accurate control over the flow volume. The pressure of the flow, however, is less accurately controlled and the variations in vacuum may result in the feel or traction of the handpiece varying during a procedure. Peristaltic and other displacement pump systems may also be somewhat slow.

Vacuum-based aspiration systems provide accurate control over the fluid pressure within the eye, particularly when combined with gravity-fed irrigation systems. While vacuum-based systems can result in excessive fluid flows in some circumstances, they provide advantages, for example, when removing a relatively large quantity of the viscous vitreous humour from the posterior chamber of the eye. However, Venturi pumps and other vacuum-based aspiration flow systems are subject to pressure surges during occlusion of the treatment probe, and such pressure surges may decrease the surgeon's control over the eye treatment procedure.

Different tissues may be aspirated from the anterior chamber of the eye with the two different types of aspiration flow. For example, vacuum-induced aspiration flow may quickly aspirate tissues at a significant distance from a delicate structure of the eye (such as the capsular bag), while tissues that are closer to the capsular bag are aspirated more methodically using displacement-induced or positive-displacement flows.

Conventionally, fluid aspiration systems include a console and a fluidic cassette mounted on the console. The fluidic cassette is typically changed for each patient and cooperates with the console to provide fluid aspiration. Generally, a single type of cassette is used by a particular console, regardless of whether the procedure will require positive displacement aspiration, vacuum-based aspiration, or both. Examples of cassettes currently used in the marketplace may be found in U.S. Pat. No. 8,070,712, U.S. Published Application 2008011431, and U.S. Published Application 20080114291, the contents of each are herewith incorporated by reference in their entirety as if set forth herein. U.S. application Ser. Nos. 14/686,582 and 13/776,988, which are hereby incorporated by reference in their entirety as if set forth herein, provide examples of cassettes.

A fluidic cassette may include means for controlling fluid flow through the cassette. In various embodiments, a fluidic cassette may include a gasket or flexible membrane located within the cassette that is configured to direct fluid flow in a predetermined flow path through the cassette. The gasket may be surrounded by front and back plates that form the body of the cassette, and the gasket may include one or more valves or a sensor that are accessible through the back plate. The surgical cassette may further include one or more tube retainers configured and dimensioned to guide a portion of either an irrigation or aspiration tube into a desired shape. The desired shape may be capable of being used with a peristaltic pump to pump fluid through the pathways formed by the gasket.

A gasket of a fluidic cassette may have a body, wherein the body is deformable and has a front surface and a back surface. The front surface may have one or more raised contours that create one or more channels that are configured and dimensioned to control fluid flow through one or more corresponding channels of a surgical cassette. The back surface may have one or more elevated portions that correspond to the one or more channels of the front surface and act as a valve. The gasket may also have a deformable membrane having an annular surface capable of coupling with a transducer of a surgical console. The console may include one or more solenoid devices that engage with the back surface of the gasket through the back plate of the cassette, thereby operating or controlling the valve of the gasket to control fluid flow in the flow pathway.

In light of the above, it would be advantageous to provide improved devices, systems, and methods for eye surgery, and more particularly for the control of fluid flow through a fluidic cassette during eye surgery.

SUMMARY OF THE INVENTION

The present invention provides a surgical cassette manifold, having a front housing, a rear housing, and a gasket, wherein the front housing comprises one or more molded fluid channels and one or more seal channels, herein the gasket is coupled with the rear housing and at least a portion of the gasket is located between the front housing and the rear housing, and wherein the gasket has one or more seal lips configured and dimensioned to couple with the one or more seal channels to form one or more fluid flow channels through the cassette. The gasket comprises one or more valves controllable through the rear housing, the valves configured to extend into the one or more fluid flow channels to reduce or block fluid flow through the flow channels.

The present invention provides a surgical cassette manifold configured to be coupled to a surgical console, the cassette manifold having a front housing, a rear housing, and a flexible gasket, wherein the gasket comprises one or more flexible flow restriction valves that reduce or block fluid flow through flow channels in the cassette, the flow restriction valves positioned along either a first flow path of irrigation fluid flowing through the cassette to a surgical handpiece or a second flow path of aspirated fluid from the surgical handpiece flowing through the cassette, or both. The flow restriction valves are actuated to reduce or block fluid flow through the first or second flow paths via one or more actuation plungers located on the surgical console. In various embodiments, the plungers may be actuated by a solenoid or other similar means to apply pressure to the flexible valves to deform the flexible valves into the flow paths.

The present invention provides a surgical cassette manifold configured to be coupled to a surgical console, the cassette manifold including a flexible gasket comprising one or more valves that reduce or block fluid flow through the surgical cassette, wherein the one or move valves are positioned adjacent a first flow path of fluid flowing into a surgical handpiece from the cassette and a second flow path of fluid flowing through the cassette that has been aspirated from the surgical handpiece. The one or more valves are actuated by an actuation plunger of the surgical console, which may be electronically controlled by a controller of the console. In various embodiments, the plungers may be actuated by a solenoid or other similar means to apply pressure to the flexible valves to deform the flexible valves into the flow paths.

In illustrative embodiments, one or more flexible valves of a surgical cassette and one or more actuation plungers of a surgical console include a positioning feature configured to assist with positioning the one or more actuation plungers to apply uniform and symmetric pressure to the one or more valves. The positioning feature includes at least two features: (i) a locking recess on a back surface of the one or more valves, the locking recess formed between two spaced-apart teeth or protrusions that extend axially away from (and are generally perpendicular to) the valve surface; and (ii) a blade tooth that extends axially away from an end surface of the plunger and is configured to be received with the locking recess to engage the valve. The positioning feature ensures the plunger is properly aligned with the flexible valve as the valve is deformed inward under pressure from the plunger.

In illustrative embodiments, a positioning feature of the surgical cassette and a surgical console may include i) a locking recess on a back surface of the one or more valves, the locking recess formed between two spaced-apart teeth or protrusions that extend axially away from (and are generally perpendicular to) the valve surface; and (ii) a blade tooth that extends axially away from an end surface of the plunger and is configured to be received with the locking recess to engage the valve. The locking recess formed by the teeth and blade tooth may be configured to be of complimentary shapes and sizes so that the blade tooth abuts against the surface of the teeth when the blade tooth is received with the locking recess. In various embodiments, a surface of the teeth may be concave in nature and a surface of the blade tooth may be convex in nature. In alternative embodiments, the positioning feature may further include an end cap on the blade tooth, the end cap include angled surfaces that correspond with tapered surfaces that further define the locking recess of the valve.

These and other advantages and features will become more apparent from the following description taken in conjunction with the drawings.

BRIEF DESCRIPTION OF THE DRAWINGS

The present invention is best understood with reference to the following detailed description of the invention and the drawings in which:

FIG. 10A is a partial side perspective view of an eye treatment console of FIG. 1, illustrating a valve actuation mechanism in the console;

FIGS. 10B1 and 10B2 are perspective views of a solenoid valve actuation member of the valve actuation mechanism of FIG. 10A, in particular, for example, for an aspiration valve and an irrigation vent valve, respectively;

DETAILED DESCRIPTION OF THE INVENTION

Reference will now be made in detail to embodiments of the invention, examples of which are illustrated in the accompanying drawings. While the invention will be described in conjunction with the embodiments, it will be understood that they are not intended to limit the invention to those embodiments. On the contrary, the invention is intended to cover alternatives, modifications, and equivalents, which may be included within the spirit and scope of the invention as defined by the appended claims.

Figure 1:
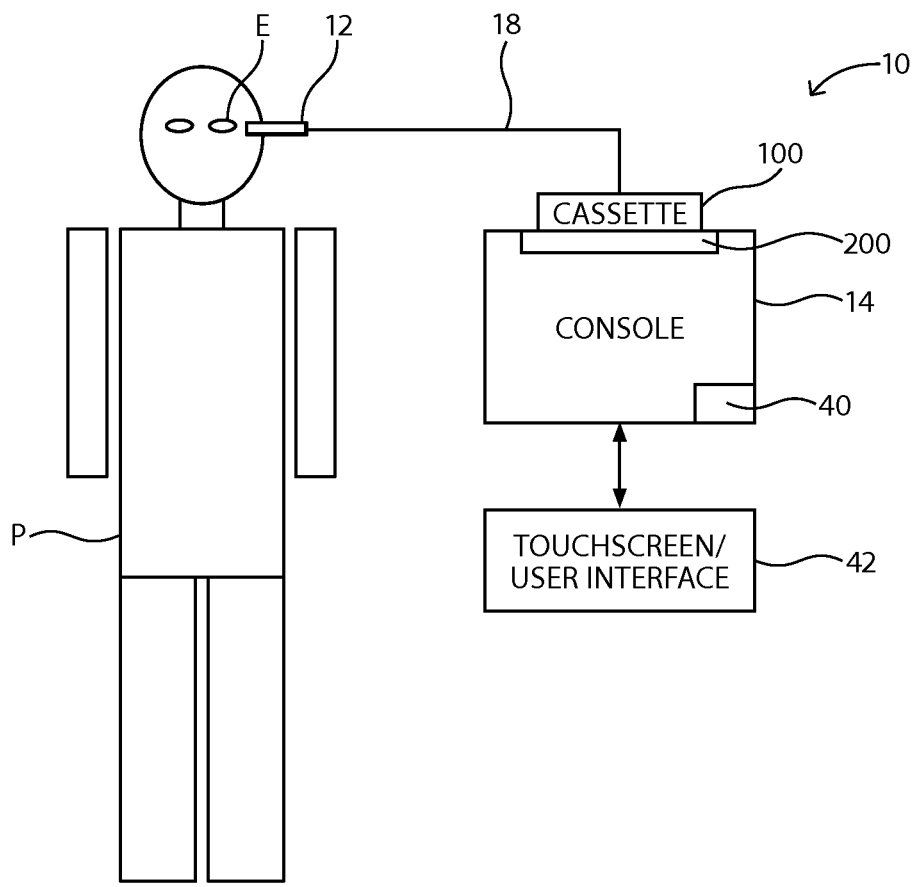
FIG. 1 schematically illustrates an eye treatment system in which a cassette couples an eye treatment probe with an eye treatment console.

Referring to FIG. 1, a system 10 for treating an eye E of a patient P generally includes an eye treatment probe handpiece 12 coupled to a console 14 by a cassette 100 mounted on the console. Handpiece 12 may include a handle for manually manipulating and supporting an insertable probe tip. The probe tip has a distal end which is insertable into the eye, with one or more lumens in the probe tip allowing irrigation fluid to flow from the console 14 and/or cassette 100 into the eye. Aspiration fluid may also be withdrawn through a lumen of the probe tip, with the console 14 and cassette 100 generally including a vacuum aspiration source, a positive displacement aspiration pump, or both to help withdraw and control a flow of surgical fluids into and out of eye E. As the surgical fluids may include biological materials that should not be transferred between patients, cassette 100 will often comprise a disposable (or alternatively, re-sterilizable) structure, with the surgical fluids being transmitted through conduits of the cassette that avoid direct contact in between those fluids and the components of console 14.

When a distal end of the probe tip of handpiece 12 is inserted into an eye E, for example, for removal of a lens of a patient with cataracts, an electrical conductor and/or pneumatic line (not shown) may supply energy from console 14 to an ultrasound transmitter of the handpiece, a cutter mechanism, or the like. Alternatively, the handpiece 12 may be configured as an irrigation/aspiration (I/A) or vitrectomy handpiece. Also, the ultrasonic transmitter may be replaced by other means for emulsifying a lens, such as a high energy laser beam. The ultrasound energy from handpiece 12 helps to fragment the tissue of the lens, which can then be drawn into a port of the tip by aspiration flow. So as to balance the volume of material removed by the aspiration flow, an irrigation flow through handpiece 12 (or a separate probe structure) may also be provided, with both the aspiration and irrigations flows being controlled by console 14.

So as to avoid cross-contamination between patients and/or to avoid incurring excessive expenditures for each procedure, cassette 100 and its conduit 18 may be disposable. Alternatively, the conduit or tubing may be disposable, with the cassette body and/or other structures of the cassette being sterilizable. Regardless, the disposable components of the cassette are typically configured for use with a single patient, and may not be suitable for sterilization. The cassette will interface with reusable (and often quite expensive) components of console 14, which may include one or more peristaltic pump rollers, a Venturi or other vacuum source, a controller 40, and the like.

Controller 40 may include an embedded microcontroller and/or many of the components common to a personal computer, such as a processor, data bus, a memory, input and/or output devices (including a touch screen user interface 42), and the like. Controller 40 will often include both hardware and software, with the software typically comprising machine readable code or programming instructions for implementing one, some, or all of the methods described herein. The code may be embodied by a tangible media such as a memory, a magnetic recording media, an optical recording media, or the like. Controller 40 may have (or be coupled to) a recording media reader, or the code may be transmitted to controller 40 by a network connection such as an internet, an intranet, an Ethernet, a wireless network, or the like. Along with programming code, controller 40 may include stored data for implementing the methods described herein, and may generate and/or store data that records parameters corresponding to the treatment of one or more patients. Many components of console 14 may be found in or modified from known commercial phacoemulsification systems from Abbott Medical Optics Inc. of Santa Ana, Calif.; Alcon Manufacturing, Ltd. of Ft. Worth, Tex.; Bausch and Lomb of Rochester, N.Y.; and other suppliers.

Figure 2A:
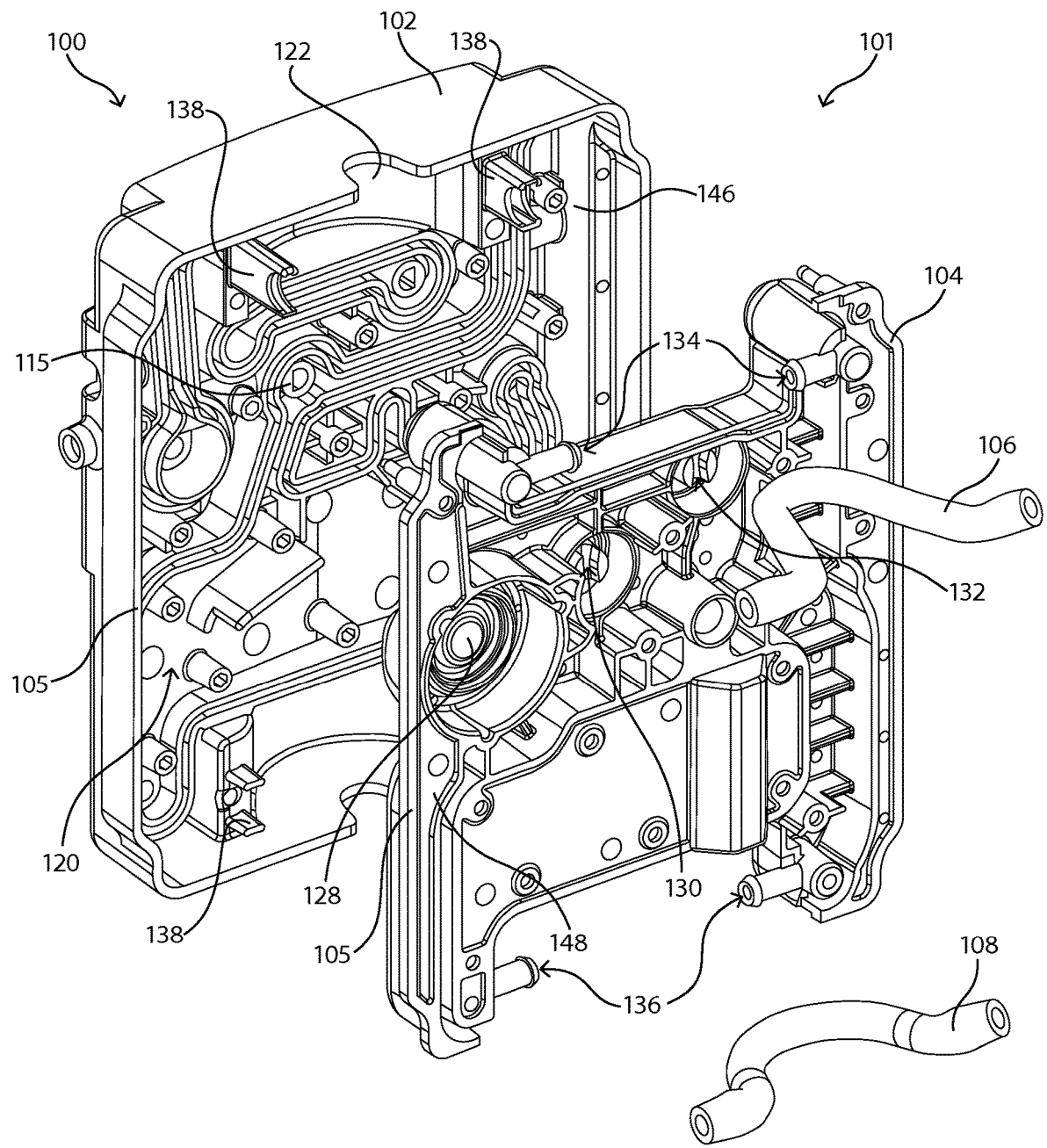
FIGS. 2A and 2B are exploded views of an exemplary surgical cassette manifold for use in the system of FIG. 1.
Figure 2B:
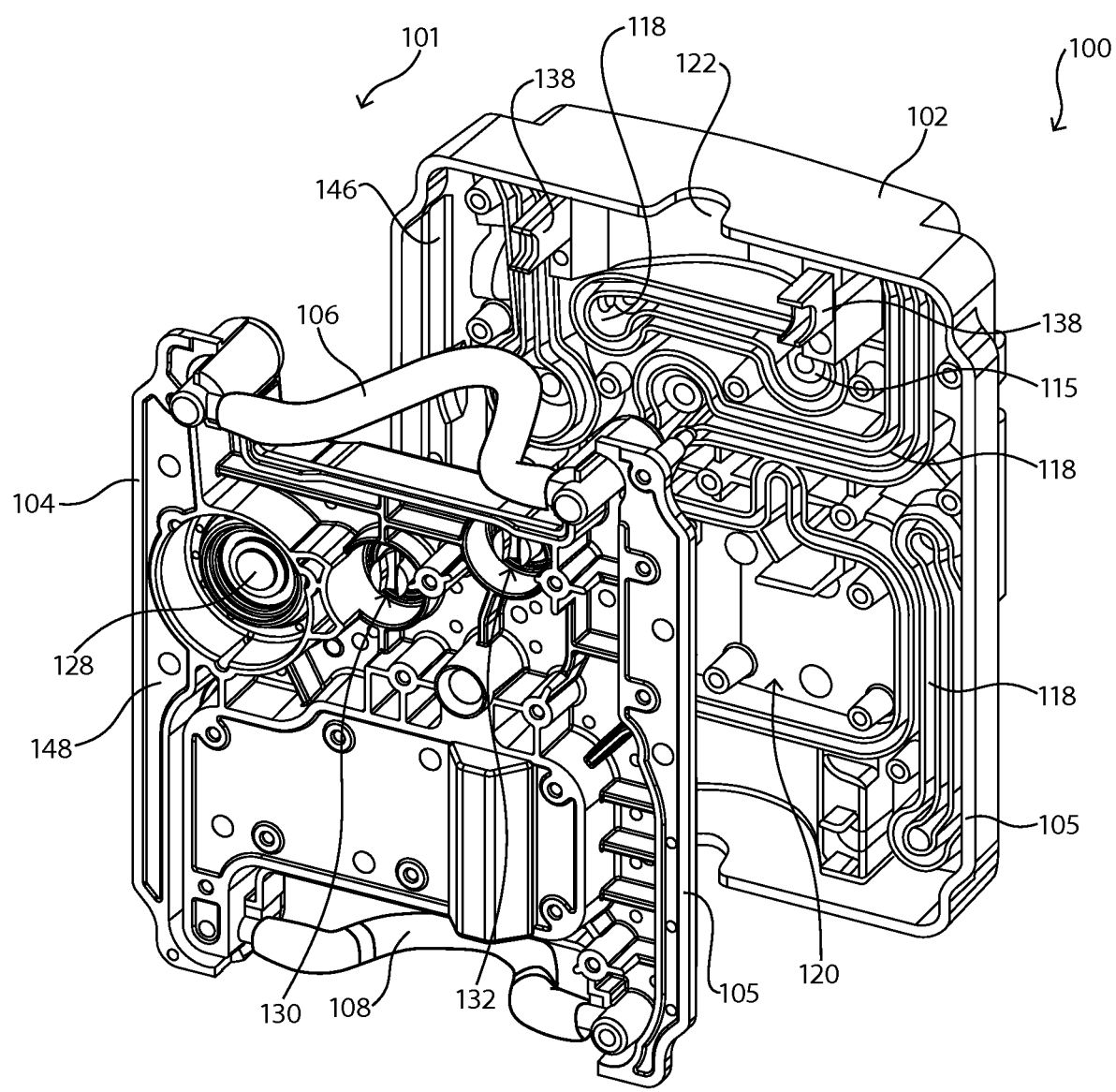

In illustrative embodiments, a surgical cassette manifold 101 is configured to be coupled and removed from the console 14 after use during a surgical procedure. FIGS. 2A and 2B illustrate a surgical cassette manifold 101 of the present invention, including components of the surgical cassette manifold 101. Cassette or surgical cassette 100 is an assembled surgical cassette manifold 101 having fluid pathways and connected tubing configured to manage one or more of the following: fluid inflow, fluid outflow, fluid vacuum level, and fluid pressure in a patient's eye E when the cassette 100 is coupled with console 14.

As shown in FIGS. 2A and 2B, the surgical cassette manifold 101 has a front housing 102, a rear housing 104, a first tubing 106, and a second tubing 108. Rear housing 104 may also have a gasket 110 co-molded or over-molded with rear housing 104. As illustrated in FIGS. 2A and 2B, the rear housing 104, the front housing 102, or a combination of both may have axial mating plane surfaces 105. Axial mating plane surfaces 105 are outer border faces of the back housing 104 and/or front housing 102 that form a surface mating with console 14 within a cassette receiver 210 of the console 14 after loading.

Figure 3B:
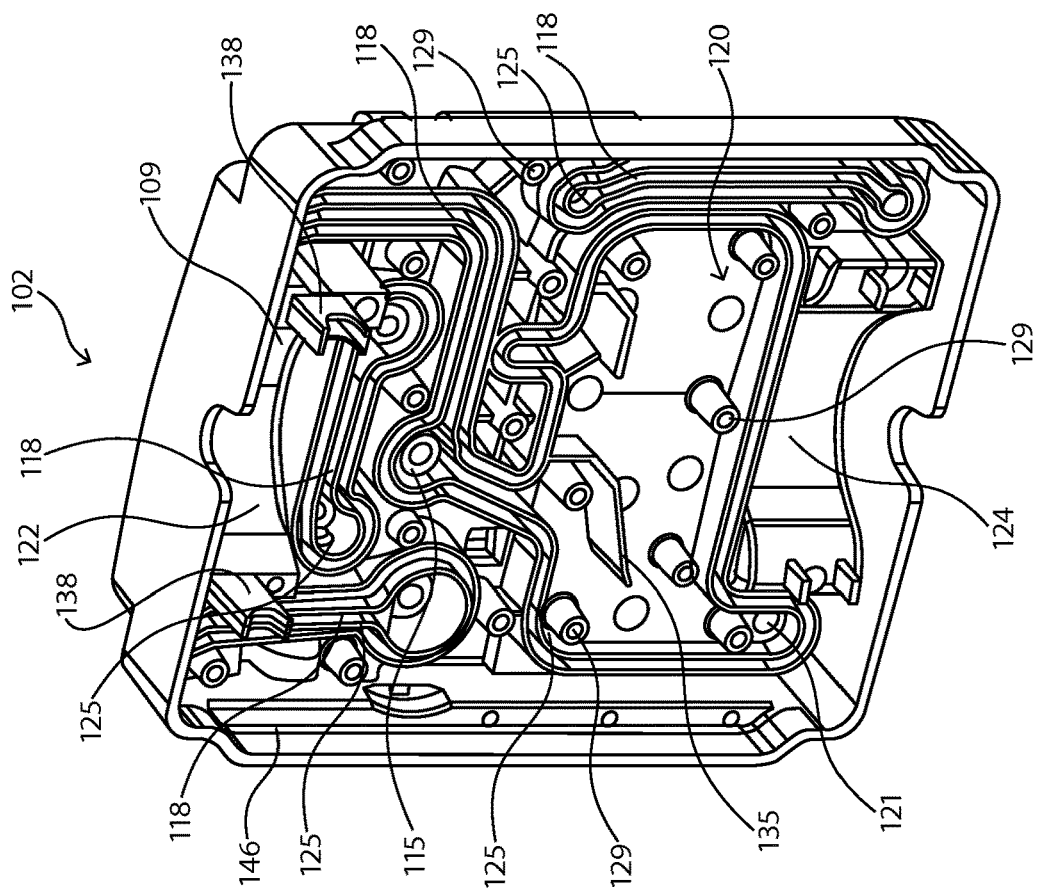
FIG. 3B is perspective back view of a front housing of an exemplary surgical cassette manifold.
Figure 3A:
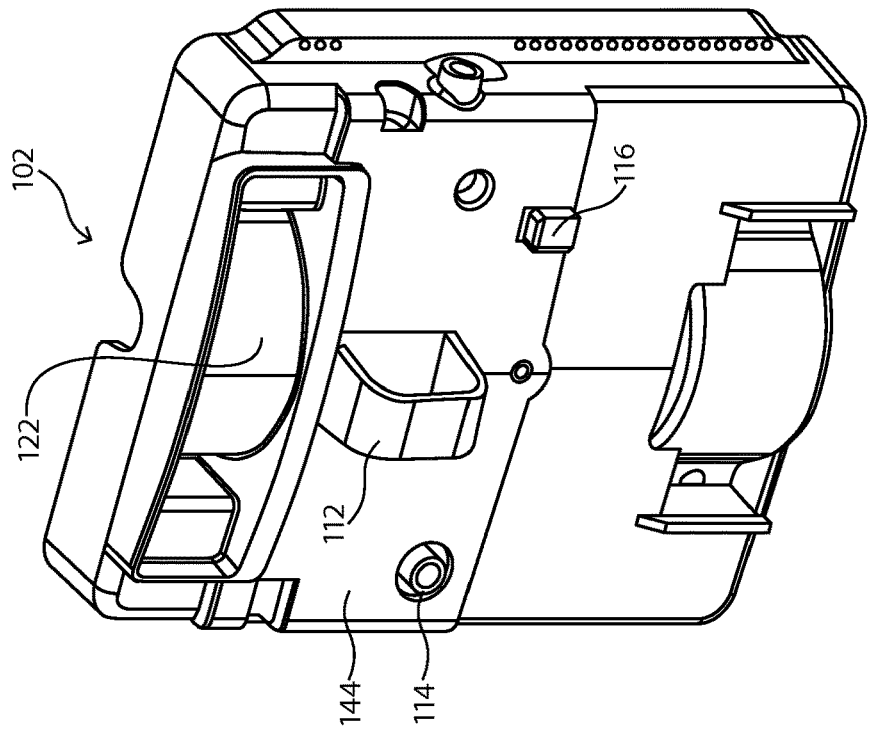
FIG. 3A is perspective front view of a front housing of an exemplary surgical cassette manifold.
Figure 11:
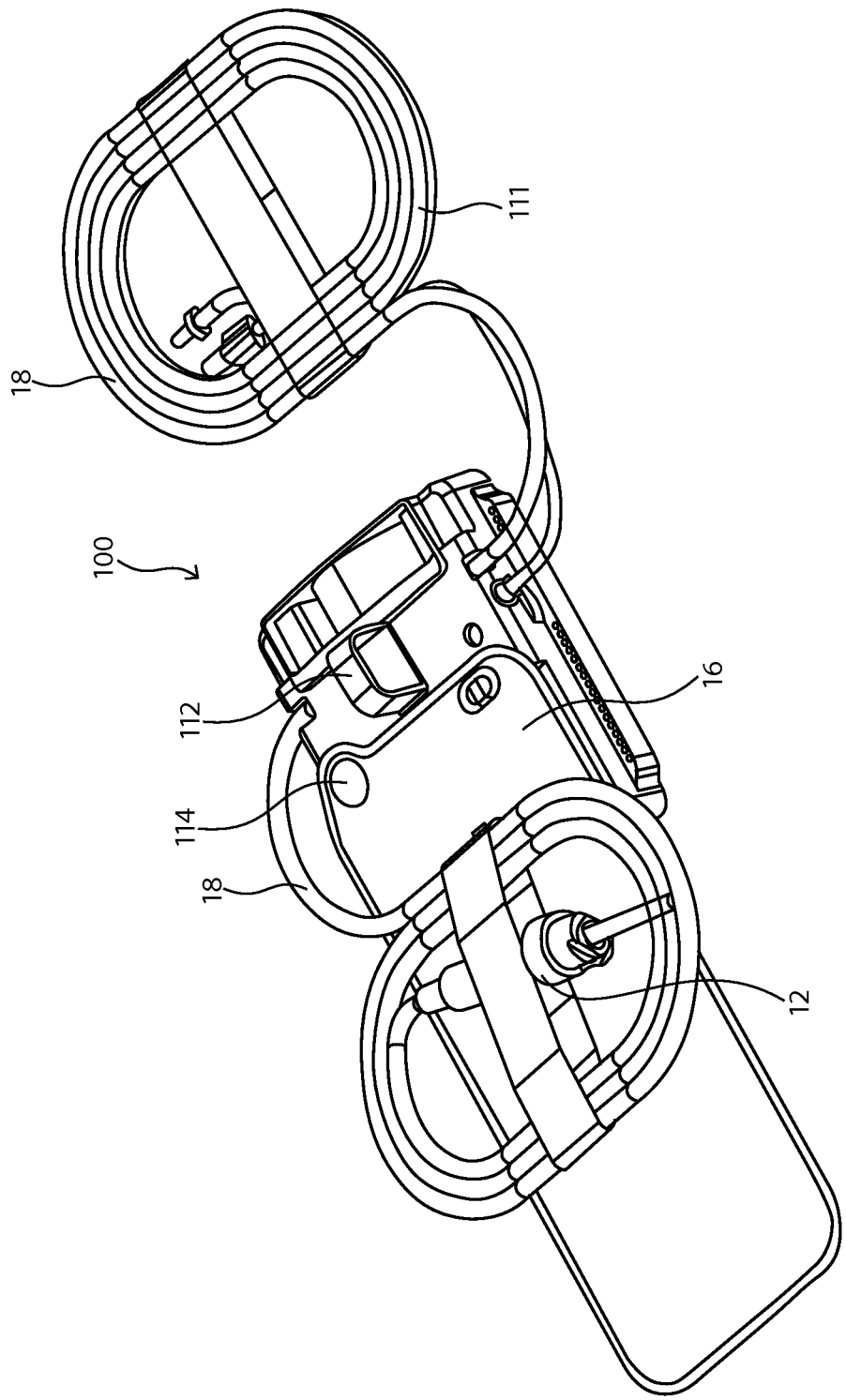
FIG. 11 is a perspective view of a surgical cassette manifold with tubes and a drainage page attached to transport fluid into or receive fluid from the cassette manifold.

FIGS. 3A and 3B illustrate the front housing 102 in more detail. FIG. 3A shows a perspective view of an illustrative embodiment of a front surface 144 of front housing 102, the front surface 144 including a handle 112 (e.g. finger grip handle), a drain port 114, and an attachment clip 116. A drain bag 16, as seen in FIG. 11, may be attached to the front surface 144 of front housing 102 via the drain port 114 and attachment clip 116 such that, when the surgical cassette 100 is coupled with the console 14 and fluid is aspirated from an eye E of a patient P, the fluid is capable of being collected in the drainage bag 16 via the drain port 114. The drain bag 16 may be supported on surgical cassette manifold 101 by the attachment clip 116 and/or drain port 114. FIG. 3B shows a perspective view of a back surface 146 of the front housing 102, the back surface 146 having in illustrative embodiments one or more molded fluid channels 118, a reservoir 120, a first pump ramp or profile 122 configured and dimensioned for mating with a peristaltic pump, and an optional second pump ramp or profile 124 configured and dimensioned for mating with a peristaltic pump.

Figure 4A:
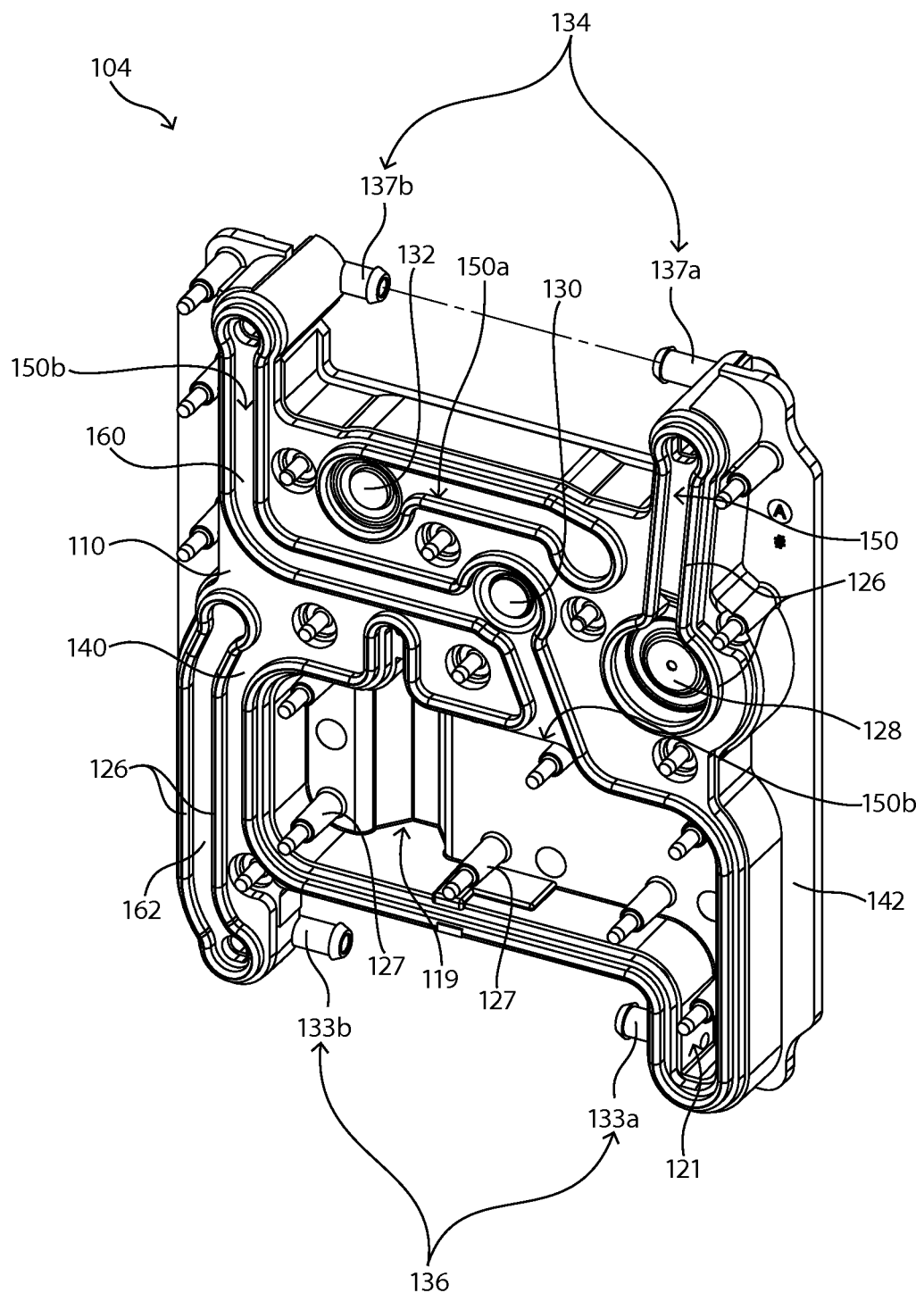
FIG. 4A is a front perspective view of a rear housing of an exemplary surgical cassette manifold.
Figure 4B:
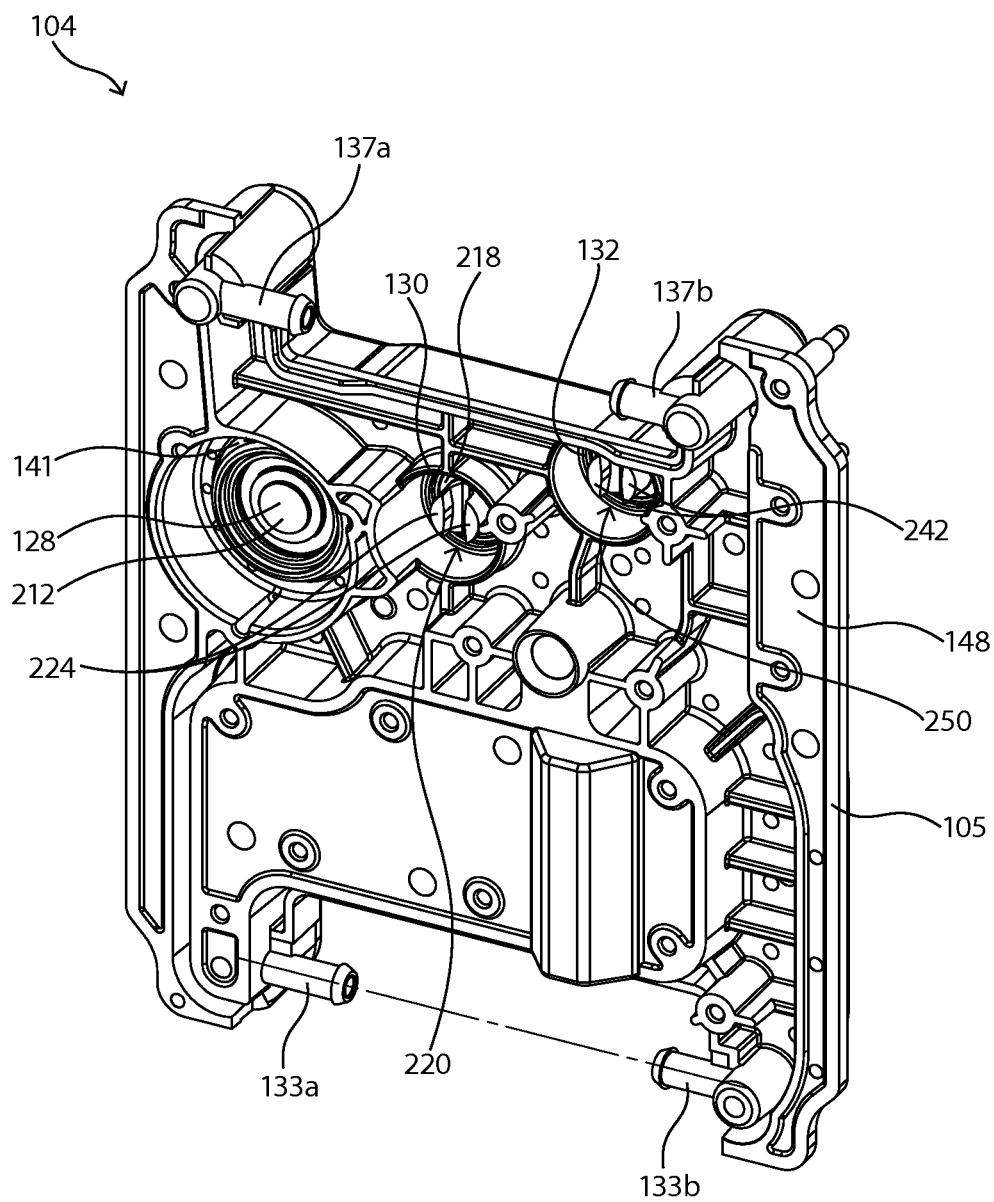
FIG. 4B is a back perspective view of a rear housing of an exemplary surgical cassette manifold.

FIGS. 4A and 4B illustrate the rear housing 104 in more detail. FIG. 4A is a front perspective view of the rear housing 104 and FIG. 4B is a back perspective view of rear housing 104. In illustrative embodiments, rear housing 104 includes a front surface 142 and a back surface 148. The rear housing 104 may include a reservoir 119, upper tube connections 134, optional lower tube connections 136, and one or more tubing retainer clips 138. In an embodiment, upper tube connections 134 are located between the front surface 142 and back surface 148 and have a slight taper from bottom toward the top so that the tubing stays on the upper tube connections 134, as illustrated in FIG. 4A. Lower tube connection 136 may similarly be located between front surface 142 and back surface 148 and have a tapered head to secure second tubing 108 to lower tube connections 136. As shown in FIG. 4A, rear housing 104 may include the gasket 110 co-molded or over-molded to it. Rear housing 104 is configured to be coupled together (for example, in a snap fit engagement) with front housing 102 to contain gasket 110 there between.

Figure 7A:
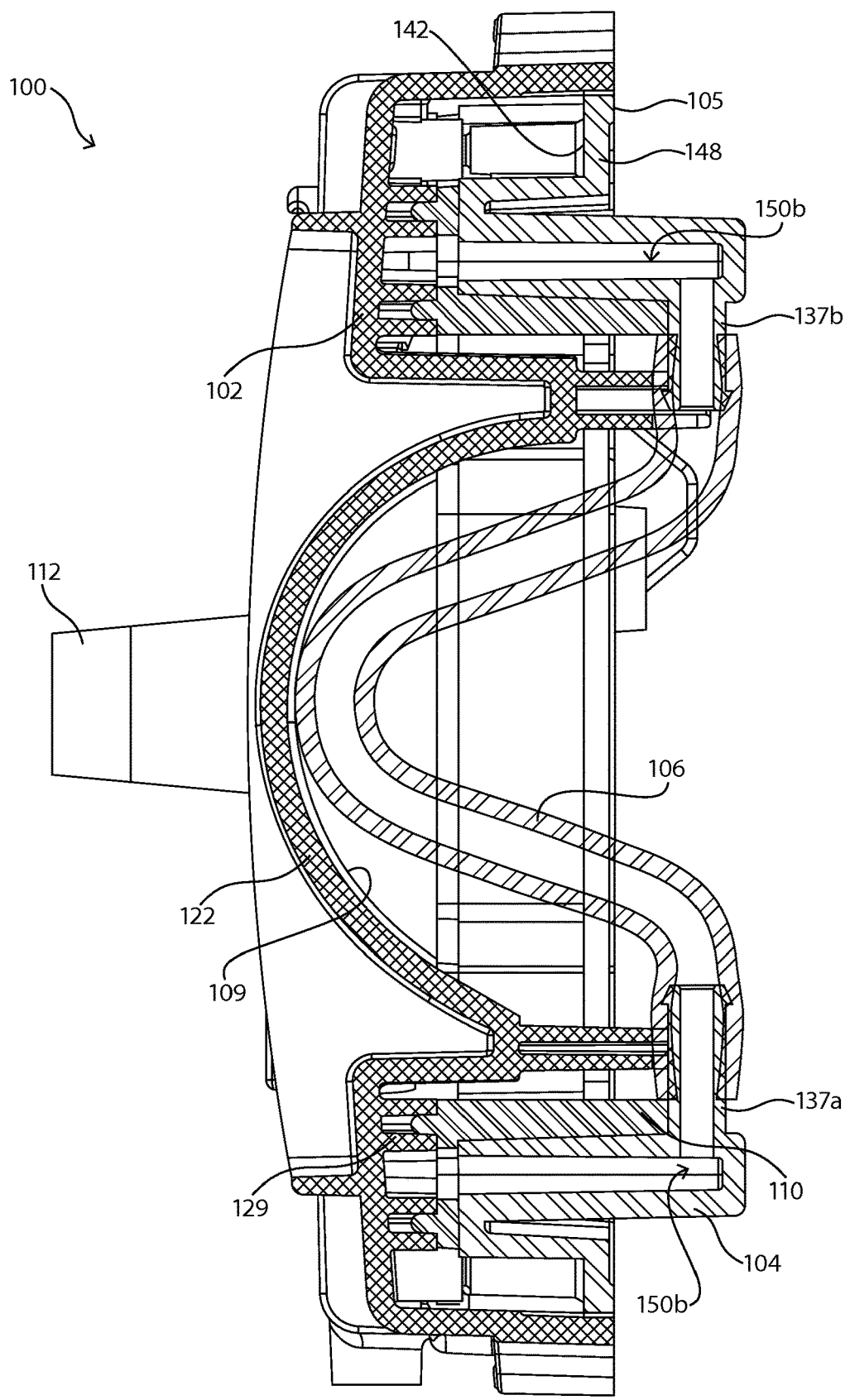
FIG. 7A is a cross-sectional view taken along the line 7A-7A in FIG. 6.

In illustrative embodiments, the surgical cassette 100 may include at least one peristaltic pump tube 106. FIGS. 2A and 2B show the backside of surgical cassette 100 and a peristaltic pump tube 106. In an embodiment, pump tube 106 may have a first end and a second end that couple with upper tube connections 134. The peristaltic pump tube 106 may be an elastomeric length of tubing that is configured to generate positive displacement of fluid flow in the direction of a pump roller (not shown) of the console 14 when a portion of the peristaltic pump tube 106 is compressed between the peristaltic pump rollers of console 14 and the ramp 122 of the front housing 102 of surgical cassette 100. It is also envisioned that any type of flow-based pump and corresponding components may be used with surgical cassette 100. In an embodiment, the ramp 122 may include a backing plate pump profile 109 comprised of contoured surfaces formed on the inside of the front housing 102 of cassette 100 to provide moving compression on the tubing 106 while creating peristaltic pumping flow through the cassette 100, particularly through pump tube 106. In various embodiments, pump tube 106 may be formed to partially conform to the shape of ramp 122, as illustrated, for example, in FIG. 7A.

In illustrative embodiments, the surgical cassette 100 may optionally include a second peristaltic pump tube 108, as illustrated in FIGS. 2A and 2B. The second pump tube 108 may be configured of similar size and shape as first pump tube 106. In an embodiment, second pump tube 108 may have a first end and a second end that couple with lower tube connections 136. Once surgical cassette manifold 101 is assembled, second tubing 108 and ramp 124 are configured to couple with a peristaltic rollers (not shown) located on console 14 to create a peristaltic pump. In an embodiment, lower tube connections 136 are on the same axis, i.e. there is axial alignment of the inflow and outflow of the second tubing 108, and maintain a specific distance apart resulting in a more accurate peristaltic pump due to a controlled length of the second tubing 108, which provides a consistent flow rate and a consistent interface with ramp 124 and peristaltic rollers. Moreover, such aligned and consistent interfaces results in less noise/sound generated by the peristaltic pump during operation. Such axial alignment may also be provided between upper tube connections 134 and first pump tube 106.

During assembly, rear housing 104 is mated with front housing 102, first tube 106 is configured to conform with first pump ramp 122, and second tube 108 is configured to conform with second pump ramp 124. First pump ramp 122 is configured and dimensioned for mating with a first peristaltic pump (not shown) located within the console 14. Second tube 108 is configured to conform with second pump ramp 124. Second pump ramp 124 is configured and dimensioned for mating with a second peristaltic pump (not shown) located within the console 14. Reservoir 120 of front housing 102 and reservoir 119 of rear housing 102 are configured to be generally aligned to create a void 117 within cassette manifold 101 defined by reservoir 120 and reservoir 119, as illustrated for example in FIG. 7C. Void 117 is configured to retain fluid pumped into cassette 100 from the handpiece 12 by the first peristaltic pump. The fluid retained in void 117 by reservoirs 119 and 120 may then be pumped out of cassette 100 to drain port 114 by the second peristaltic pump.

In illustrative embodiments, reservoir 120 may have a sump 121. Sump 121 is a portion of reservoir 120 that extends below a bottom 120*c* of reservoir 120 that promotes fluid to flow from the reservoir 120 to sump 121 and to the lower tube connection 136. Sump 121 may (1) reduce turbulence of the tank; and (2) ensure a drain inlet port 133*a* of the lower tube connection 136 is always below the level of fluid inside the void 117, therefore fluid is consistently pumped out of the cassette 100 and not air (which may cause the drain bag 16 to balloon).

In illustrative embodiments, tubing retainer clips 138 (shown in FIGS. 2A and 2B) may be provided to protrude substantially perpendicularly from a plane of the back side 122 of front housing 102 to secure the first pump tube 106. Tubing retainer clips 138 are configured and dimensioned to assist with easy assembly of surgical cassette manifold 101 and maintaining first tubing 106 in a specific orientation after assembly. Similar tubing retainer clips 138 may be positioned to retain second pump tube 108.

In illustrative embodiments, gasket 110 may be over-molded with back housing 104 such that gasket 110 is secured to back housing 104, and gasket 110 is further configured to be sandwiched between front housing 102 and back housing 104 when the cassette 100 is assembled together. As shown in FIG. 3B, front housing 102 also may have one or more seal channels 125. Seal channels 125 may be configured and dimensioned to mate with gasket 110. Specifically, seal channels 125 may be configured and dimensioned to mate with a seal lip 126 that extends outwardly or perpendicularly from a front surface 140 of gasket 110. Seal lip 126 is a part of gasket 110 configured to create a seal or lid over molded fluid channels 118 of front housing 102. The seal lip 126 may have any dimension suitable for mating with seal channel 125. In an embodiment, seal lip 126 may be tapered, starting thicker at its proximal end and becoming thinner towards its distal end. In another embodiment, seal lip 126 may be slightly larger than seal channel 125 to create a snug fit. Seal lip 126 provides positioning alignment on front housing 102 and rear housing 104.

Figure 5:
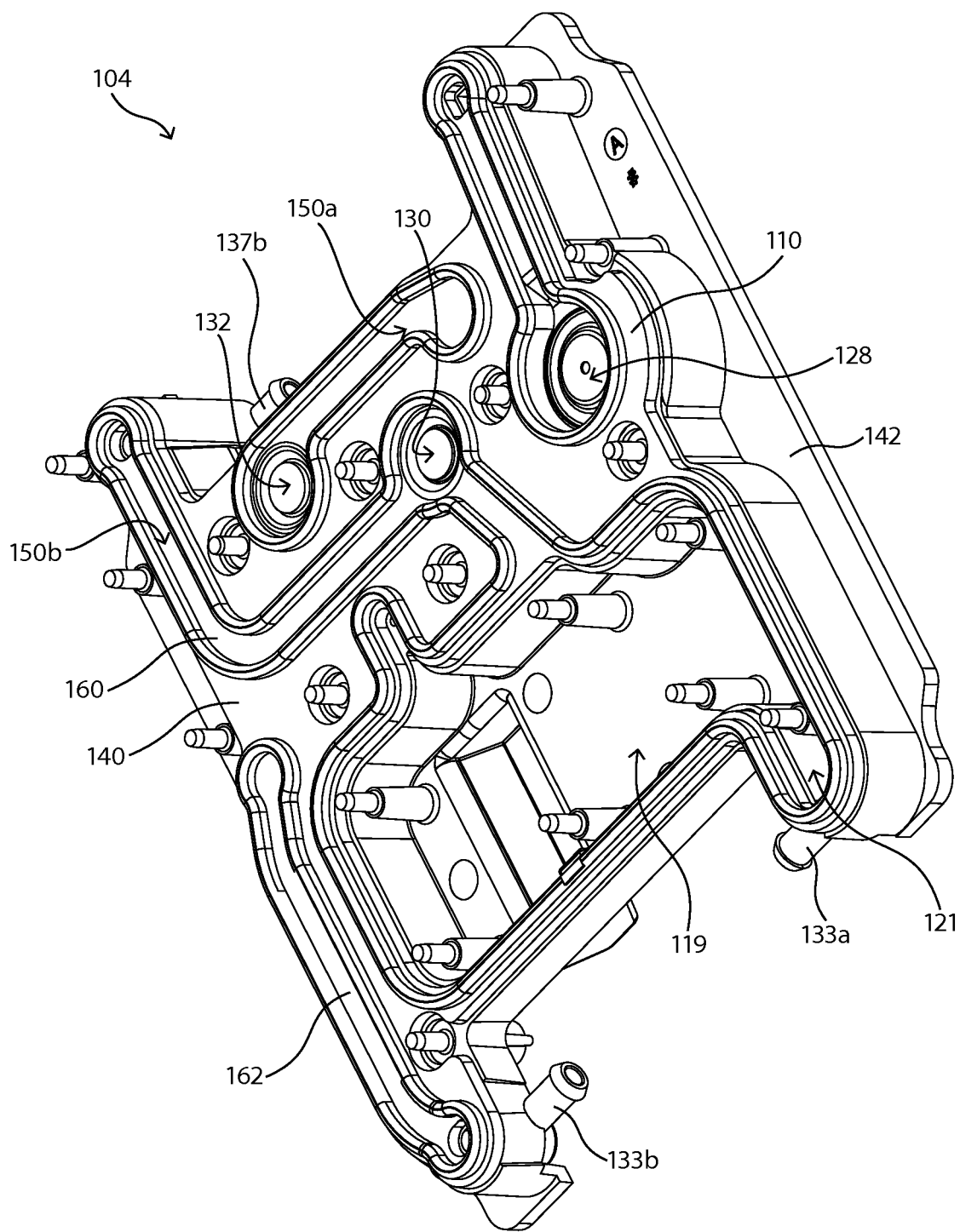
FIG. 5 is a side view of the front side of the rear housing illustrated in FIG. 4A.

Gasket 110 may be formed separately from rear housing 104 and then co-molded or over-molded onto rear housing 104. Gasket 110 includes a front surface 140 and a back surface 141 such that the front surface 140 is adjacent the front housing 102 and the back surface 141 is adjacent the rear housing 104 when the front housing 102 is coupled to the rear housing 104. The front surface 140 of gasket 110 includes the seal lip 126 which extends away or protrudes in a substantially perpendicular direction from a plane of gasket 110 and rear housing 104, as illustrated in FIGS. 4A and 5. Gasket 110 may include a pressure/vacuum sensor diaphragm 128, an aspiration vent valve 130, and/or an irrigation valve 132, discussed in more detail below.

In an embodiment, gasket 110 may be molded, co-mold, or two-shot molded onto or with rear housing 104. Molding gasket 110 onto rear housing 104 in such a manner reduces or eliminates a leak path which is possible with molded fluid channels when using two different materials. In an embodiment, a method of eliminating leaking of molded fluid channels by combining two different materials for creating a proper seal is envisioned resulting in an easier manufacturing method by creating a self-aligning gasket 110. In an alternative embodiment, when assembling rear housing 104 to front housing 102, mating of seal lip 126 and seal channel 125 can be achieved using a plurality of alignment pins 127 on rear housing 104 that mate with counterpart pin holes 129 on front housing 102, as illustrated in FIGS. 3B and 4A. Using alignment pins 127 and pin holes 129 as opposed to relying only on the flexible seal lip 126 and seal channel 125 allows for an easier and more efficient assembly process. Molding gasket 110 onto or with rear housing 104 results in pre-alignment/pre-keyed/pre-orientation of seal lip 126 for properly sealing with molded fluid channels 118 on front housing 102, thus reducing or even eliminating leaking and increasing ease of manufacture.

In illustrative embodiments, when gasket 110 is properly placed between front housing 102 and rear housing 104, and front and rear housings 102 and 104 are coupled together, molded fluid channels 118 of front housing 102 and portions of the gasket 110 between the seal lips 126 form at least one sealed flow channel or pathway 150 through the cassette 100. Referring to FIGS. 4A and 4B, sealed flow channel 150 includes one or more fluid flow pathways formed by raised surfaces (e.g. seal channels 125 of front housing 102) allowing fluid to flow in internal channels between the raised surfaces and outer perimeter sealing (e.g. seal lips 126) border of gasket 110 to retain fluid within the manifold fluid flow channels 118 under positive pressure and vacuum conditions. Accordingly, the sealed flow channel 150 directs the flow of fluids through the cassette manifold 101 as the peristaltic pumps operate. Sealed flow channel 150 is generally in fluid communication with fluid reservoir 120. The sealed flow channel 150, comprising of the molded fluid channels 118 and gasket 110, accordingly eliminates the need for tubing to transport fluid through the cassette 100.

In various embodiments, sealed flow channel 150 may include an irrigation flow channel 150a and an aspiration flow channel 150b. Irrigation flow channel 150a is configured as a pathway with an inlet tubing port (not shown) from a balance salt solution (BSS) irrigation bottle (not shown) metered by one or more irrigation valves to one or more of the following: (1) an irrigation tubing outlet port (not shown) connected to an external surgical handpiece 12 flowing fluid to the eye, which may be metered or controlled by irrigation valve 132; or (2) a venting line (not shown) providing BSS irrigation fluid into the aspiration flow channel 150b. In various embodiments, irrigation flow channel 150a may be positioned within cassette 100 to transport fluid that is driven into the cassette 100 from a gravity-driven irrigation bottle, through the cassette 100, and to the external handpiece 12 to provide irrigation fluid to the surgical field. In illustrative embodiments, fluid may be transported into the cassette 100 via an irrigation tube 111, as illustrated in FIG. 11. Other means of flow for irrigation fluid through a cassette and to a handpiece 12 are known in the art.

Aspiration flow channel 150b is configured as a pathway for fluid to flow from the external handpiece 12 to the drainage port 114 after the fluid or other particles have been aspirated from a patient's eye E. In illustrative embodiments, during aspiration of a patient's eye E, fluid flows through the aspiration flow channel 150b in various manners. For instance, fluid may flow into the first pump tube 106 via a pump tube inlet 137a. Upper tube connections 134 of rear housing 104 may comprise pump tube inlet 137a and pump tube outlet 137b to transport fluid from pump tube inlet 137a, through the first pump tube 106, and then through the pump tube outlet 137b as the first peristatic pump operates. In illustrative embodiments, aspiration flow channel 150b extends from pump tube outlet 137b to transport fluid through the cassette manifold 101. Aspiration flow channel 150 extends from pump tube outlet 137b to reservoir 120 along a first pathway 160, as illustrated in FIGS. 4A and 5. Fluid is therefore transported into reservoir 120 via first pathway 160. Fluid may be transported out of reservoir 120 via a drain pump inlet port 133a. Lower tube connections 136 may comprise drain pump inlet port 133a and a drain pump outlet 133b to transport fluid from drain pump inlet port 133a, through the second pump tube 108, and then through the drain pump outlet port 133b as the second peristatic pump operates. Drain pump outlet 133b is coupled with a drain bag 16 to allow fluid to be removed from reservoir 120 via the second peristaltic pump, as illustrated in FIGS. 4A and 5. Illustratively, a second pathway 162 of flow channel 150 runs in a vertical direction from a lower tube connection 136 (that is fluidly connected to the second tubing 108 associated with a second peristaltic pump) to drain port 114 out to the drain bag 16. Other configurations of an aspiration flow channel 150b are envisioned within the scope of this disclosure.

The aspiration flow channel 150b may further include a venting port for venting fluid inflow from a BSS irrigation bottle or the irrigation flow channel 150a, which may be metered into the aspiration flow channel 150b by the aspiration vent valve 130. Aspiration vent valve 130 is configured to permit introduction of irrigation fluid into the aspiration flow channel 150b, which may be metered by vent valve 130, to, for example, reduce vacuum level in the aspiration flow channel 150b. Such reduction of vacuum level may be necessary following obstruction or occlusion of the tip of handpiece 12 by, for example, particles being aspirated from the eye E.

Figure 6:
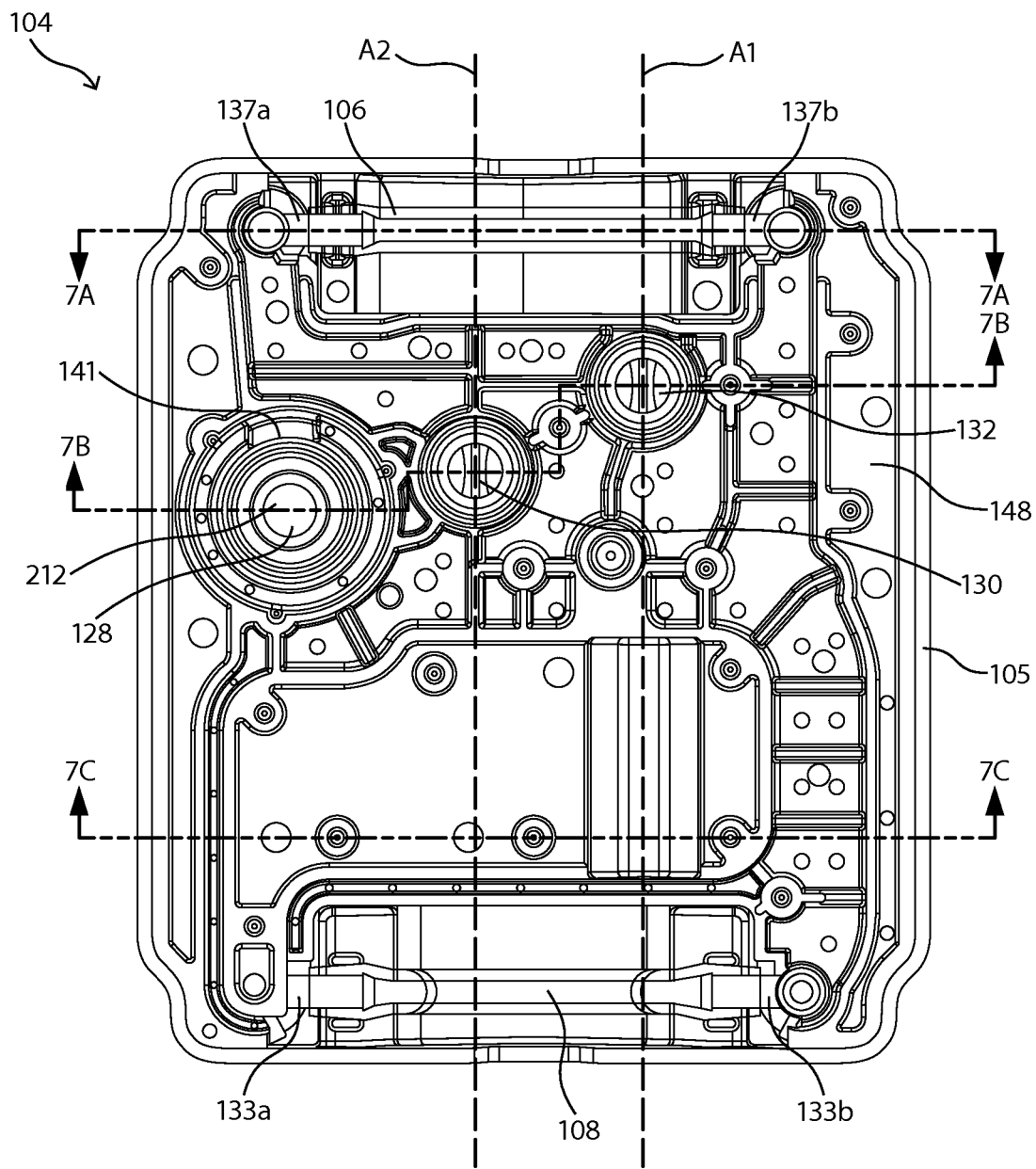
FIG. 6 is a back perspective view of the rear housing illustrated in FIG. 4B.

In illustrative embodiments, to monitor and control the flow of fluid through the sealed flow channel 150, the cassette 100 may include a pressure/vacuum sensor diaphragm 128, a aspiration vent valve 130, and/or an irrigation valve 132, as illustrated in FIG. 6. Specifically, the pressure/vacuum sensor diaphragm 128, aspiration vent valve 130, and/or irrigation valve 132 may be formed within the gasket 110. The gasket 110 adjacent the aspiration flow channel 150b may include the vacuum/pressure sensor diaphragm 128 and aspiration vent valve 130, and the gasket 110 adjacent the irrigation flow channel 150a may include the irrigation valve 132.

Figure 10C:
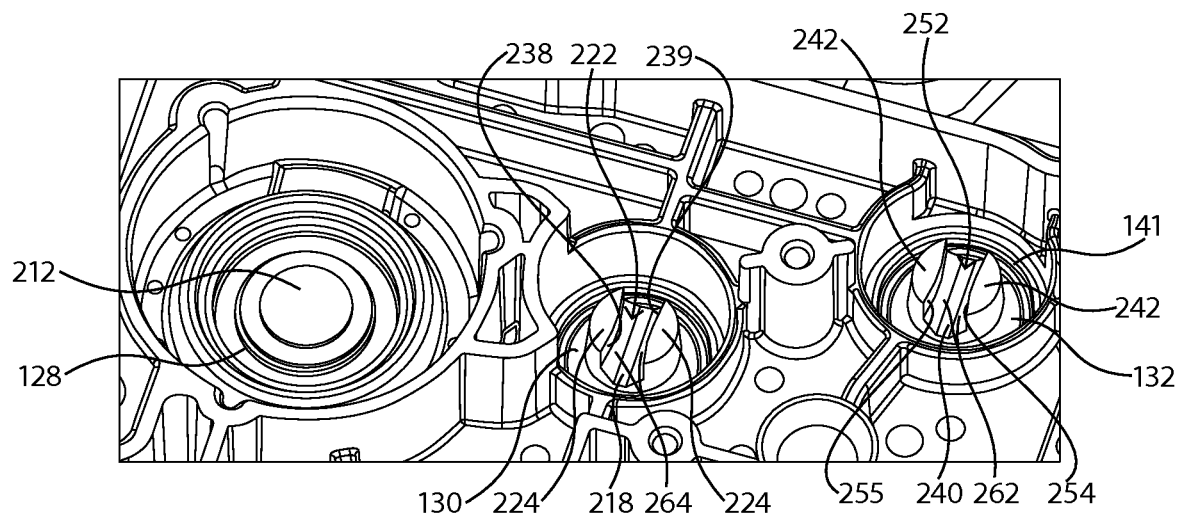
FIG. 10C is a partial back perspective view of the valve assembly of FIG. 4B.

In illustrative embodiments, vacuum/pressure sensor diaphragm 128 may be a sealed flexible annular membrane with a central magnetic coupling disk 212. The vacuum/pressure sensor diaphragm 128 may be positioned to be in fluid connection with the aspiration flow channel 150b. The central magnetic coupling disk 212 deforms: (1) proportionally outwards under fluid pressure conditions in the aspiration flow channel 150b, compressing a magnetically-coupled force displacement transducer 208 of console 14 (as illustrated in FIG. 10A); and (2) proportionally inwards under fluid vacuum conditions in the aspiration flow channel 150b, extending a magnetically-coupled force displacement transducer 208 of console 14. Such deformation of the vacuum/pressure sensor diaphragm 128 allows for non-fluid contact measurement of fluid vacuum levels of the aspiration flow channel 150b of surgical cassette manifold 101.

Referring to FIGS. 4A and 4B, irrigation valve 132 of surgical cassette 100, which in an embodiment may have a dome-like shape, may be an elastomeric deformable surface which allows irrigation flow from a BSS bottle to external surgical handpiece 12 when uncompressed and shuts off flow in the irrigation flow channel 150a when the irrigation valve 132 deforms into the irrigation flow channel 150a (towards the front housing 102). Similarly, aspiration vent valve 130, which in an embodiment may have a dome-like shape, may be an elastomeric deformable surface which allows irrigation flow (from the BSS bottle or irrigation flow channel 150a) into the aspiration flow channel 150b that is coupled with the external surgical handpiece 12. When irrigation fluid is introduced into the aspiration flow channel 150b, the vacuum level of the aspiration flow channel 150b, and accordingly the vacuum level of aspiration occurring in the patient's eye E, is reduced. In various embodiments, the reduction could be such that aspiration flow is shut off when the aspiration vent valve 130 is deformed into fluid channels 118 (towards the front housing 102). Accordingly, the level of fluid flow in the sealed fluid flow channel 150 may be controlled based upon the level of compression of valves 130 and 132—from full flow to intermediate flow to no flow.

In an illustrative embodiment, as illustrated in FIGS. 3A and 3B, surgical cassette 100 may have one or more valve control surfaces 115. Valve control surfaces 115 may be a raised sealing surface in manifold fluid flow channels 118 of front housing 102 that provide a point of contact for valve 130 or 132 when they are deformed or activated toward the fluid flow channels 118 of front housing 102.

The interaction between the console 14 and cassette 100 will now be described. In illustrative embodiments, a fluidics module 200 according to an embodiment of the present invention comprises an assembly of components mounted to the console 14 for interfacing with the surgical cassette 100, as illustrated in FIG. 10A. A fluidics module 200 may have one or more of the following components: (i) a cassette receiver 210, (ii) a cassette pre-load detection pin, and/or (iii) a pre-load detection switch. For instance, a cassette receiver 210 may be a section of fluidics module 200 defining an engagement area for loading and aligning surgical cassette 100 in its intended position relative to various components of fluidics module 200. In other embodiments, fluidics module 200 may have one or more pump roller assemblies (not shown) configured with multiple roller elements in a circular or substantially circular pattern which produce peristaltic flow-based fluid transport when rotated against compressed fluid-filled peristaltic pump tubes 106 and 108. Other components of a fluidics module are generally known in the art and may be incorporated into the fluidics module 200 of the present disclosure to assist with interfacing the surgical cassette 100 with the console 14.

In illustrative embodiments, fluidics module 200 may have a force displacement transducer 208. Force displacement transducer 208 may be electrically or otherwise connected with the controller 40. Force displacement transducer 208 may operate by means of a magnetic coupling (via, for example, a magnet 214) with the central magnetic coupling disk 212 of the vacuum/pressure sensor diaphragm 128. Specifically, a vacuum occurrence of fluid inside the aspiration flow channel 150b formed by manifold fluid flow channels 118 will cause deformation inwards of the vacuum/pressure sensor diaphragm 128 (and the magnetic coupling disk 212) in the surgical cassette 100, and the magnetic force from the coupling disk 212 upon the magnet 214 of the force displacement transducer 208 will axially extend force displacement transducer 208 outward away from the fluidics module 200, resulting in a change of an electrical output signal to the controller 40 in proportion to a vacuum level. Conversely, positive fluid pressure in the aspiration flow channel 150a formed by manifold fluid flow channels 118 results in an outward extension of vacuum/pressure sensor diaphragm 128 and compression of the force displacement transducer 208 inward toward the fluidics module 200.

In an embodiment, fluidics module 200 may have an irrigation valve plunger 230 and an aspiration vent valve plunger 232. Irrigation valve plunger 230 axially extends away from the fluidics module 200 and is controlled (e.g. by a solenoid (not shown) in the console 14) to move in a direction towards or away from the fluidics module 200 when controlled by the controller 40. The irrigation valve plunger 230 is configured to compress the irrigation valve 132 of surgical cassette 100, resulting in a decrease or shutoff of irrigation flow in the irrigation flow channel 150a to external irrigation tubing line to the handpiece 12. Irrigation valve plunger 230 may also operate by a spring-loaded retraction of the plunger to allow varying levels of irrigation flow. Similarly, vent valve plunger 232 may be controlled by controller 40 and have an axial extension of the plunger 232 that compresses aspiration vent valve 130 of surgical cassette 100, resulting in a decrease or shutoff of irrigation venting flow to the aspiration flow channel 150b. Aspiration vent valve plunger 232 may also operate by a spring-loaded retraction of the plunger to allow irrigation pressure fluid flow to vent in aspiration flow channel 150b if the pressure/vacuum level requires reduction.

The irrigation valve plunger 230 and aspiration vent plunger 232 are configured with an end surface 234 and 236, respectively, that are configured to deform the irrigation valve 132 and aspiration vent valve 130, respectively, to block flow of fluid through the flow channel 150 positioned next to the irrigation valve 132 and aspiration vent valve 130. Specifically, for example, when the irrigation valve plunger 230 and the aspiration vent plunger 232 are engaged into the flow channel 150, the end surfaces 234 and 236 may be configured to contact or seal with the back surface 146 of the front housing 102, reducing or completely stopping the flow of fluid through the flow channel 150. In illustrative embodiments, the end surface 234 and 236 may abut against the valve control surfaces 115 (having the irrigation valve 132 and aspiration vent valve 130 sealing with the valve control surfaces 115) to reduce or eliminate flow of fluid.

In illustrative embodiments, the end surfaces 234 and 236 and the valves 132 and 130 are generally configured to be similar in size and shape, in order for the end surfaces 234 and 236 to deform the valves 132 and 130. As the end surfaces 234 and 236 engage with the valves 132 and 130, it is desirable to avoid any potential for asymmetrical loading or otherwise deforming the valves in such a way that would compromise the sealing. Further, by ensuring an evenly distributed load distribution, the overall force required upon the plunger (e.g. by the solenoid) may be reduced to a minimal level required to engage the valves.

In illustrative embodiments, the irrigation valve plunger 230 and irrigation valve 132 are configured with a positioning feature 250 to avoid asymmetrical loading upon the valve 132,—as illustrated in FIGS. 6, 9A, 9B, 10A, 10B2 and 10C, for example. Positioning feature 250 includes a locking recess 252 on a back surface 240 of irrigation valve 132, the locking recess 252 being positioned along the back surface 141 of gasket 110. Locking recess 252 is formed between two spaced-apart teeth 242 of positioning feature 250 that extend axially away from (and are generally perpendicular to) the back surface 240, as illustrated for example in FIGS. 6, 7B, 9A, 9B, and 10C. Positioning feature 250 further includes a blade tooth 246 that extends axially away from the end surface 234 of the irrigation valve plunger 230. In illustrative embodiments, blade tooth 246 is configured to be received with the locking recess 252 formed by the spaced-apart teeth 242 and to engage with the irrigation valve 132. As the irrigation valve plunger 230 engages with the irrigation valve 132, blade tooth 246 may abut against the back surface 240 of the irrigation valve 132 between the spaced-apart teeth 242. Accordingly, positioning feature 250 ensures irrigation valve plunger 230 is properly aligned with irrigation valve 132 as irrigation valve plunger 230 is moved toward irrigation valve 132, for uniform contact therewith, and further permits irrigation valve 132 to be deformed uniformly by irrigation valve plunger 230 when irrigation valve plunger 230 applies force to irrigation valve 132. Locking recess 252 and blade tooth 246 may be generally each aligned along a first axis A1.

Figure 7B:
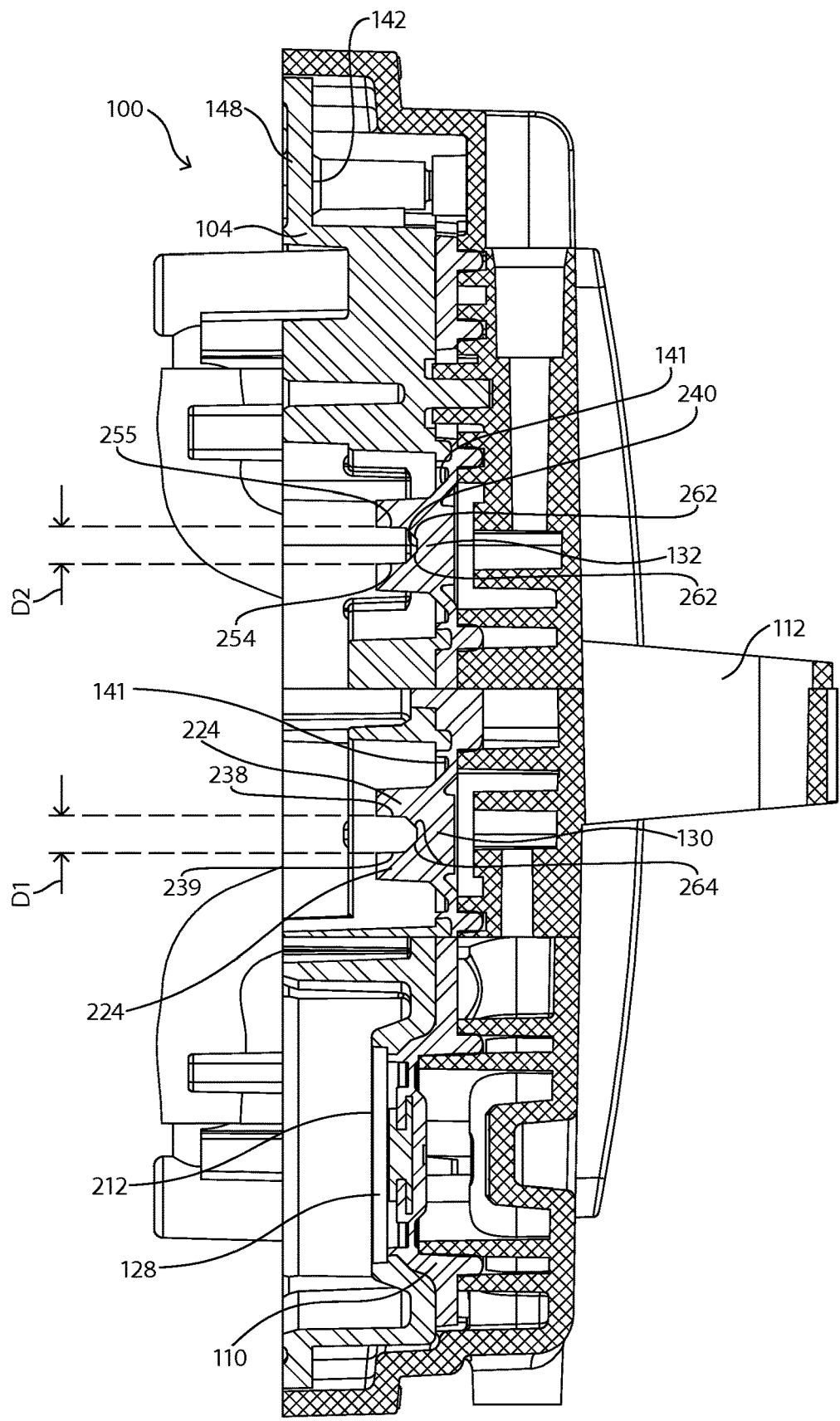
FIG. 7B is a cross-sectional view taken along the line 7B-7B in FIG. 6.
Figure 7C:
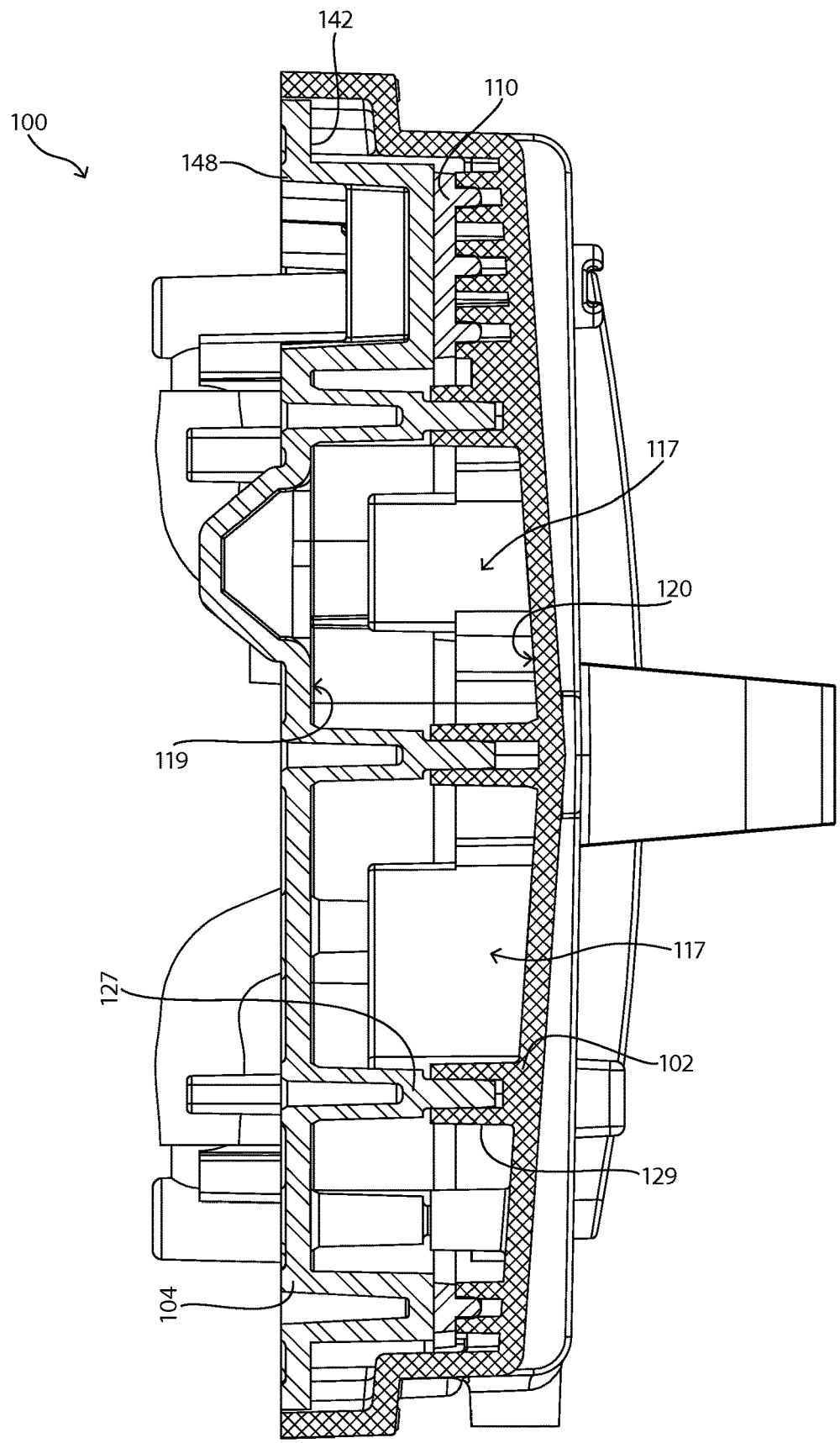
FIG. 7C is a cross-sectional view taken along the line 7C-7C in FIG. 6.
Figure 9A:
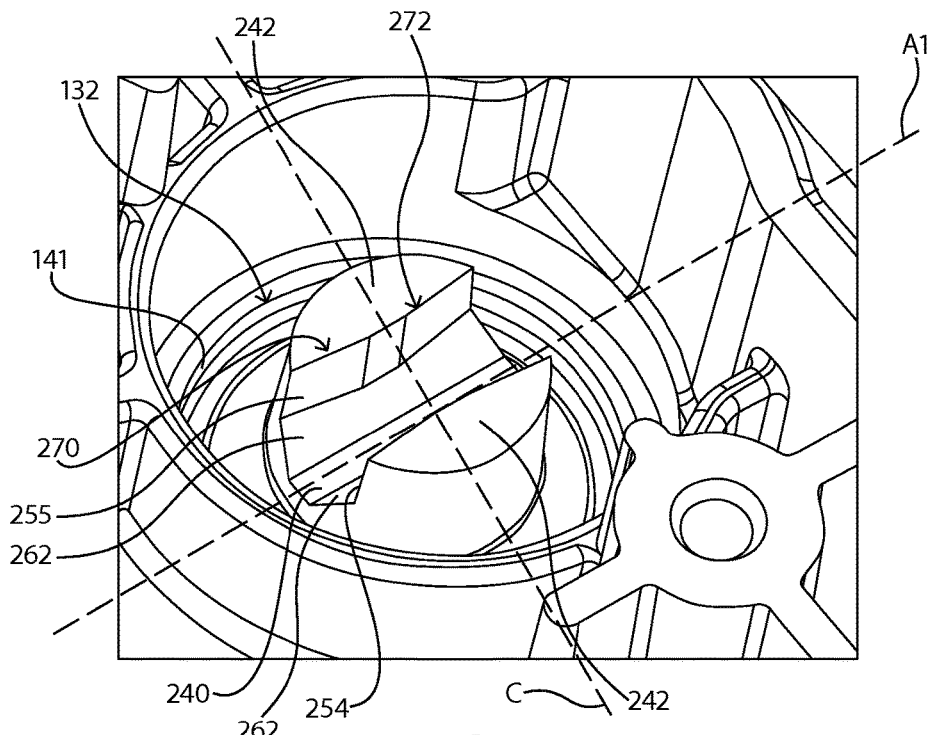
FIG. 9A is a side perspective view of a valve assembly of the surgical cassette manifold of FIG. 4B.

In illustrative embodiments, and as illustrated in FIG. 10B2, blade tooth 246 may include a first contact surface 248 and a second contact surface 249. Similarly, as illustrated in FIGS. 7B and 9A, spaced-apart teeth 242 may include first and second receiving surfaces 254 and 255. As blade tooth 246 is received within locking recess 252, first contact surface 248 may engage with or abut against first receiving surface 254, and second contact surface 249 may engage with or abut against second receiving surface 255.

Figure 8:
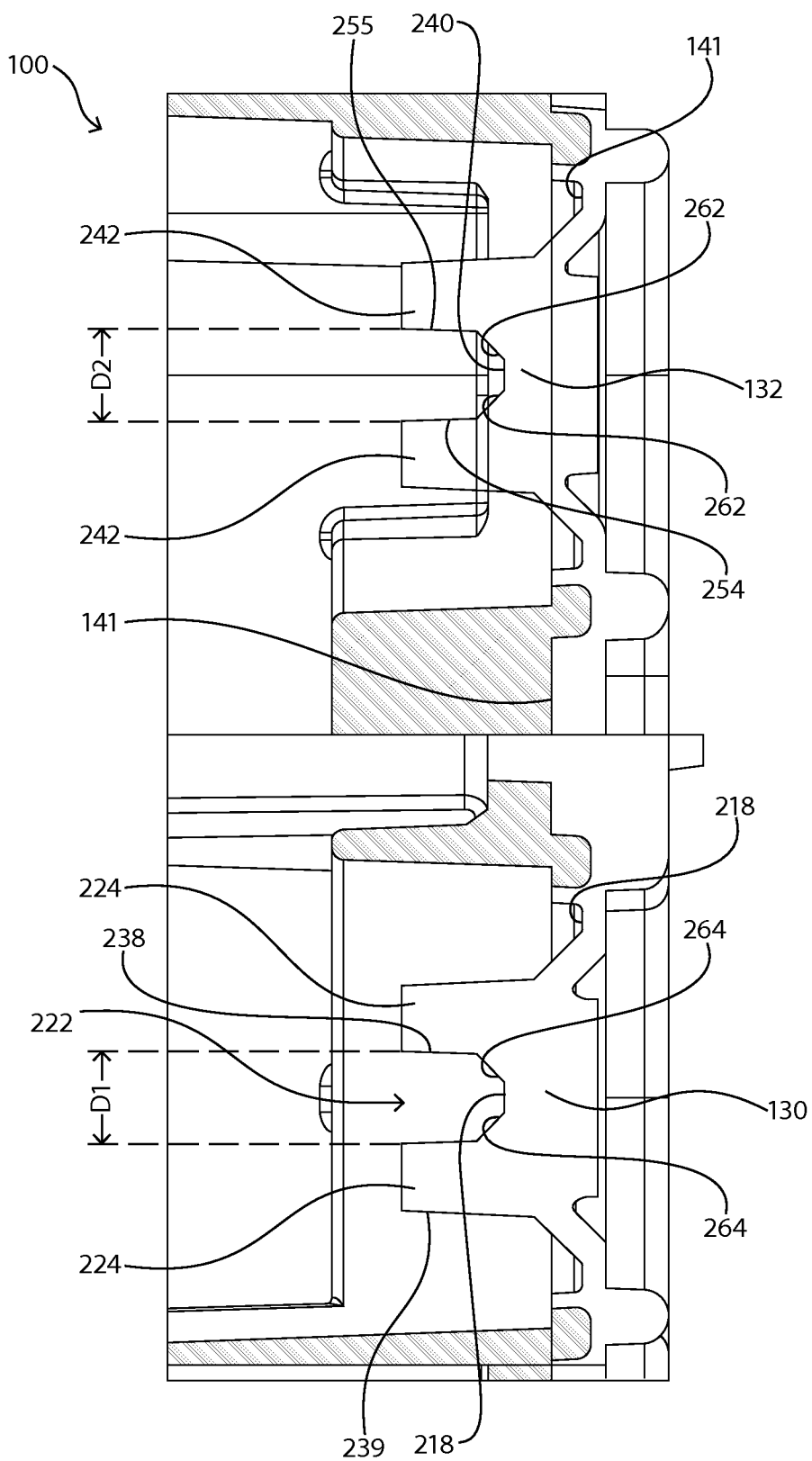
FIG. 8 is a cross-sectional view of one or more valve assemblies of the surgical cassette manifold of FIG. 4B.
Figure 9B:
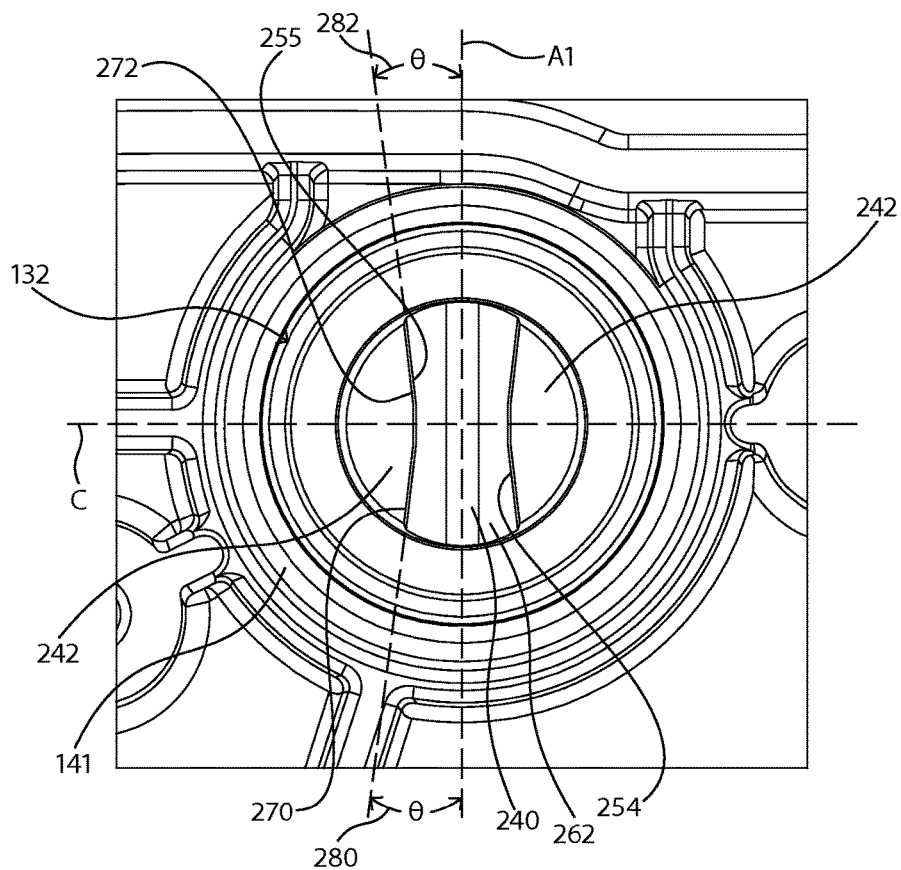
FIG. 9B is a top perspective view of a valve assembly of the surgical cassette manifold of FIG. 4B.

First contact surface 248, second contact surface 249, first receiving surface 254, and second receiving surface 255 may be configured in a variety of shapes or sizes. For instance, first contact surface 248 may exist is a single plane P1, and second contact surface 249 may exist in a single plane P2, where plane P1 is parallel to plane P2, as illustrated in FIG. 10B2. First and second receiving surface 254 and 255 may mirror first and second contact surfaces 248 and 249 and each exist in a single plane. Alternatively, first contact surface 248 may be convex or concave in nature, and second contact surface 249 may be oppositely convex or concave in nature. First and second receiving surfaces 254 and 255 may again mirror the first and second contact surfaces 248 and 249 to abut against the convex or concave first and second contact surfaces 248 and 249, as illustrated in FIGS. 9A and 9B. Other shapes or forms of first contact surface 248, second contact surface 249, first receiving surface 254, and second receiving surface 255 are envisioned herein. First and second receiving surfaces 254 and 255 may be spaced apart distance D2, as illustrated in FIGS. 7B and 8, to receive blade tooth 246.

In illustrative embodiments, first receiving surface 254 may include a first angled portion 270 and a second angled portion 272, where the first angled portion 270 extends from a bottom circumference surface of the teeth 242 to generally a center axis C of the teeth 242, and the second angled portion 272 extends from a top circumference surface of the teeth 242 to generally the center axis C, as illustrated in FIGS. 9A and 9B. As illustrated in FIG. 9B, first angled portion 270 may extend at a first angle 280 from axis A1, and second angled portion 272 may extend at a second angle 282 from axis A1, whereby the second angle 282 is different than the first angle 280. Accordingly, the teeth 242 may be shaped differently along the first angled portion 270 and second angled portion 272. In another embodiment, the first angle 280 and the second angle 282 may be similar or the same.

In illustrative embodiments, blade tooth 246 may further include an end cap 256 that is configured to further guide blade toot into locking recess 252. In an exemplary embodiment, as illustrated in FIG. 10B2, end cap 256 may include tapered sides 258. Tapered sides 258 may engage with and abut against corresponding tapered surfaces 262 that extend between the back surface 240 of the irrigation valve and first and second receiving surfaces 254 and 255.

In illustrative embodiments, the aspiration vent valve plunger 232 and aspiration vent valve 130 are configured with a positioning feature 220 respectively, to avoid asymmetrical loading upon the valve 130, as illustrated for example in FIGS. 10A, 10B1, 10C and 10D. The positioning feature 220 may be substantially similar to the positioning feature 250 described above. For instance, positioning feature 220 includes a locking recess 222 on a back surface 218 of aspiration vent valve 130, the locking recess 222 being positioned along the back surface 141 of gasket 110. Locking recess 222 is formed between two spaced-apart teeth 224 of positioning feature 220 that extend axially away from (and are generally perpendicular to) the back surface 218, as illustrated for example in FIGS. 6, 7B, 8, 9A, and 10C. Positioning feature 220 further includes a blade tooth 226 that extends axially away from the end surface 236 of the aspiration vent valve plunger 232. In illustrative embodiments, blade tooth 226 is configured to be received with the locking recess 222 formed by the spaced-apart teeth 224 and to engage with the aspiration vent valve 130. As the aspiration vent valve plunger 232 engages with the aspiration vent valve 130, blade tooth 226 may abut against the back surface 218 of the aspiration vent valve 130 between the spaced-apart teeth 224. Accordingly, positioning feature 220 ensures aspiration vent valve plunger 232 is properly aligned with aspiration vent valve 130 as aspiration vent valve plunger 232 is moved toward aspiration vent valve 130, for uniform contact therewith, and further permits aspiration vent valve 130 to be deformed uniformly by aspiration vent valve plunger 232 when aspiration vent valve plunger 232 applies force to aspiration vent valve 130. Locking recess 222 and blade tooth 226 may be generally each aligned along a second axis A2.

In illustrative embodiments, blade tooth 226 may include a first contact surface 228 and a second contact surface 229. Similarly, spaced-apart teeth 224 may include first and second receiving surfaces 238 and 239. As blade tooth 226 is received within locking recess 222, first contact surface 228 may engage with or abut against first receiving surface 238, and second contact surface 229 may engage with or abut against second receiving surface 239.

First contact surface 228, second contact surface 229, first receiving surface 238, and second receiving surface 239 may be configured in a variety of shapes or sizes. For instance, first contact surface 228 may exist is a single plane P1, and second contact surface 229 may exist in a single plane P2, where plane P1 is parallel to plane P2. First and second receiving surface 238 and 239 may mirror first and second contact surfaces 228 and 229 and each exist in a single plane. Alternatively, first contact surface 228 may be convex or concave in nature, and second contact surface 229 may be oppositely convex or concave in nature. First and second receiving surfaces 238 and 239 may again mirror the first and second contact surfaces 228 and 229 to abut against the convex or concave first and second contact surfaces 228 and 229. Other shapes or forms of first contact surface 228, second contact surface 229, first receiving surface 238, and second receiving surface 239 are envisioned herein. First and second receiving surfaces 238 and 239 may be spaced apart distance D1, as illustrated in FIGS. 7B and 8, to receive blade tooth 246. Distance D1 may be smaller than, the same as, or larger than distance D2, depending on the design of the valves 130 and 132 and the cassette 100.

Figure 10D:
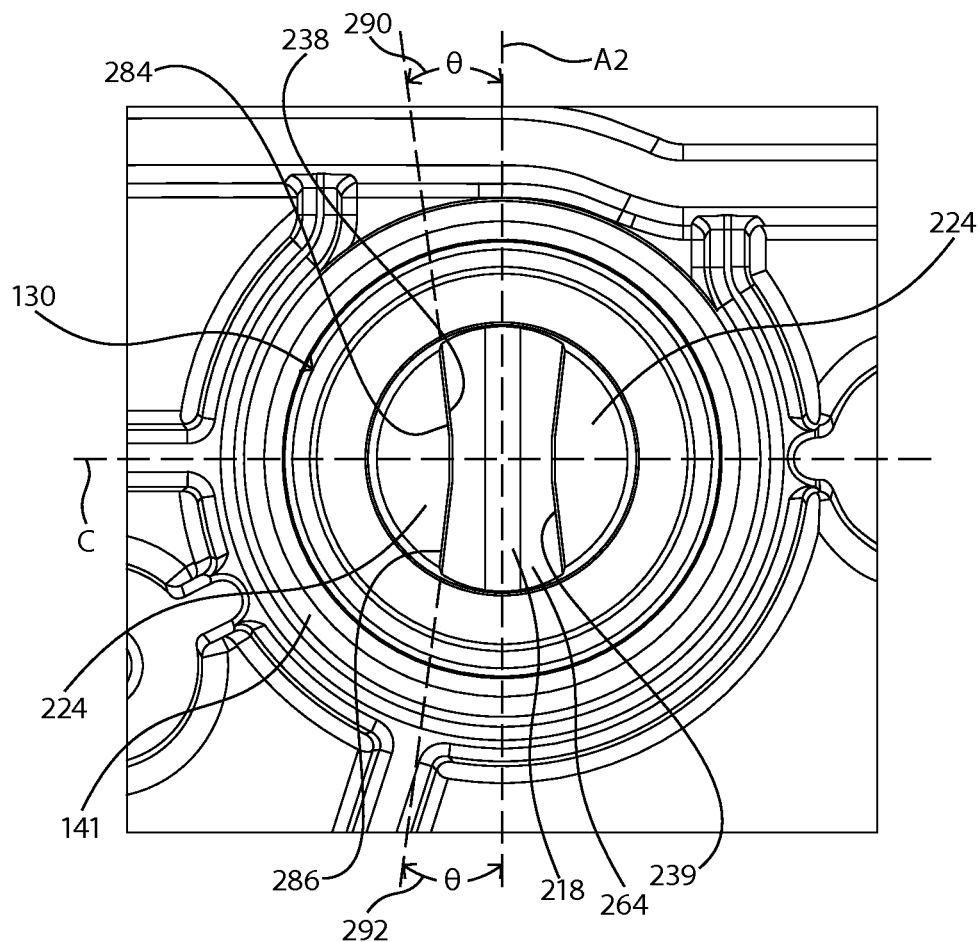
FIG. 10D is a top perspective view of an alternative valve assembly of the surgical cassette manifold of FIG. 4B.

In illustrative embodiments, first receiving surface 238 may include a first angled portion 284 and a second angled portion 286, where the first angled portion 284 extends from a bottom circumference surface of the teeth 224 to generally a center axis C of the teeth 224, and the second angled portion 286 extends from a top circumference surface of the teeth 224 to generally the center axis C. As illustrated in FIG. 10D, first angled portion 284 may extend at a first angle 290 from axis A2, and second angled portion 286 may extend at a second angle 292 from axis A2, whereby the second angle 292 is different than the first angle 290. Accordingly, the teeth 224 may be shaped differently along the first angled portion 284 and second angled portion 286.

In illustrative embodiments, blade tooth 226 may further include an end cap 274 that is configured to further guide blade tooth into locking recess 222. In an exemplary embodiment, as illustrated in FIG. 10B1, end cap 274 may include tapered sides 276. Tapered sides 276 may engage with and abut against corresponding tapered surfaces 264 that extend between the back surface 218 of the vent valve 130 and first and second receiving surfaces 238 and 239.

In illustrative embodiments, blade tooth 226 may be fixedly coupled to a rectangular base 260 that is retained within the console 14, as illustrated in FIG. 10B1. The base 260 may be configured to be received within a similarly-shaped aperture (not shown) of console 14 to prevent or reduce unintended rotation of blade tooth 226, thereby preventing or reducing misalignment with the locking recess 222.

In an embodiment, surgical cassette manifold 101 may be made substantially of a plastic material except for gasket 110. The plastic material may be acrylonitrile-butadiene-styrene (ABS), polycarbonate (PC), polyethylene, viton, or other rigid plastic or plastic material. In addition, the material may be such that it is transparent enabling a user to visualize various features of surgical cassette manifold 101. For example, all components may be transparent, including reservoir 120. In an embodiment, one or more lights emitted from console 14 may be shone through surgical cassette manifold 101 to provide a backlight and allow a user to visualize the fluid flow as it flows from handpiece 12 through sealed fluid flow channel 150 into reservoir 120 and out to the drain bag 16. In an embodiment, the backlight may also be used as a surgical cassette manifold type detector.

All references cited herein are hereby incorporated by reference in their entirety including any references cited therein.

Although the present invention has been described in terms of specific embodiments, changes and modifications can be carried out without departing from the scope of the invention which is intended to be limited only by the scope of the claims.

The invention claimed is:

1. A surgical cassette, comprising:
a front plate;
a back plate; and
a gasket comprising one or more deformable valves, the one or more deformable valves including a back surface and spaced-apart teeth coupled to the back surface and extending in an axial direction from the back surface, the spaced apart teeth forming a locking recess including a first receiving surface including at least one first angled portion and a second receiving surface including at least one second angled portion, the spaced-apart teeth or the back surface configured to receive a force to deform the one or more valves, wherein the front plate and back plate together surrounds at least a portion of the gasket, and wherein the spaced-apart teeth extend through an aperture in the back plate, and
the gasket is coupled to the front plate to permit the one or more valves to engage with a surface of the front plate when the one or more valves are deformed.

2. The surgical cassette of claim 1, wherein a back surface of the gasket abuts against the back plate.

3. The surgical cassette of claim 2, wherein the one or more valves are accessible through the back plate.

4. The surgical cassette of claim 1, wherein the front plate and gasket form a flow channel for fluid to flow through the cassette.

5. The surgical cassette of claim 4, wherein the one or more deformable valves are configured to restrict or block flow of fluid through the flow channel.

6. The surgical cassette of claim 4, wherein the flow channel transports fluid aspirated from a surgical field and the one or more deformable valves is configured to restrict or block flow of fluid through the flow channel.

7. The surgical cassette of claim 6, wherein the fluid is transported through the cassette via a peristaltic pump.

8. The surgical cassette of claim 4, wherein the flow channel transports fluid flowing into an irrigation pathway of the cassette via the force of gravity from an irrigation source.

9. The surgical cassette of claim 8, wherein the one or more deformable valves is a valve to vent fluid from the irrigation source into an aspiration pathway of the cassette.

* * * * *